(12) United States Patent
Hagen et al.

(10) Patent No.: US 10,146,973 B2
(45) Date of Patent: Dec. 4, 2018

(54) SYSTEMS AND METHODS FOR READING MACHINE-READABLE LABELS ON SAMPLE RECEPTACLES

(71) Applicant: Gen-Probe Incorporated, San Diego, CA (US)

(72) Inventors: Norbert D. Hagen, Carlsbad, CA (US); David Opalsky, San Diego, CA (US); Rolf Silbert, Del Mar, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 0 days.

(21) Appl. No.: 15/092,150

(22) Filed: Apr. 6, 2016

(65) Prior Publication Data

US 2016/0328588 A1    Nov. 10, 2016

Related U.S. Application Data

(60) Provisional application No. 62/143,963, filed on Apr. 7, 2015.

(51) Int. Cl.
*G06K 7/10* (2006.01)
*G01N 35/00* (2006.01)
(Continued)

(52) U.S. Cl.
CPC ... *G06K 7/10732* (2013.01); *G01N 35/00732* (2013.01); *G01N 35/026* (2013.01);
(Continued)

(58) Field of Classification Search
CPC ... G01N 35/00732; G01N 2035/00752; G01N 35/026; G01N 2035/00801;
(Continued)

(56) References Cited

U.S. PATENT DOCUMENTS 5,754,632 A * 5/1998 Smith ............... G06Q 20/26
                                                        379/114.14
8,055,546 B1 * 11/2011 Cassone ............ G06Q 30/02
                                                        705/7.29

(Continued)

FOREIGN PATENT DOCUMENTS

EP    2080553 A1    7/2009

OTHER PUBLICATIONS

PCT, Internal Search Report and Written Opinion, International Application No. PCT/US2016/026237, dated Sep. 13, 2016.

*Primary Examiner* — Thien M Le
(74) *Attorney, Agent, or Firm* — Charles B. Cappellari; Brian S. Sun; Kyle E. Conklin

(57) ABSTRACT

Systems for reading machine-readable labels, for example, two-dimensional barcodes, include a housing, a reader configured to read the machine-readable labels on sample receptacles as a sample rack holding the sample receptacles move between a first position and a second position within the housing. The system includes a processing and control unit configured to decode a read image of the machine-readable labels on each sample receptacle, and configured to associate a decoded read images with the corresponding sample receptacles based on measured positions of the sample rack when the machine-readable label was read.

27 Claims, 18 Drawing Sheets

(51) Int. Cl.
*G01N 35/02* (2006.01)
*G06K 7/14* (2006.01)
*G06K 19/06* (2006.01)
*G01N 35/04* (2006.01)

(52) U.S. Cl.
CPC ...... *G06K 7/10811* (2013.01); *G06K 7/10861* (2013.01); *G06K 7/1413* (2013.01); *G06K 7/1417* (2013.01); *G06K 7/1447* (2013.01); *G06K 19/06028* (2013.01); *G06K 19/06037* (2013.01); *G01N 2035/00752* (2013.01); *G01N 2035/00801* (2013.01); *G01N 2035/00831* (2013.01); *G01N 2035/00851* (2013.01); *G01N 2035/0413* (2013.01); *G01N 2035/0493* (2013.01)

(58) Field of Classification Search
CPC . G01N 2035/00831; G01N 2035/0491; G01N 35/00603; G01N 2035/00782; G06Q 10/087; G06K 19/06028; G06K 7/10732; G06K 7/10811
USPC .............................. 235/462.11, 375, 462.25
See application file for complete search history.

(56) References Cited

U.S. PATENT DOCUMENTS

| | | | |
|---|---|---|---|
| 8,112,306 B2* | 2/2012 | Lyerly | G06Q 10/00 705/7.38 |
| 2001/0048029 A1* | 12/2001 | Kitagawa | G06K 7/10683 235/462.43 |
| 2002/0035543 A1* | 3/2002 | Shedd | G06Q 20/04 705/44 |
| 2004/0031852 A1* | 2/2004 | Boitsov | G06K 19/06037 235/472.03 |
| 2005/0002828 A1* | 1/2005 | Gunji | B01L 3/0217 422/400 |
| 2005/0036913 A1 | 2/2005 | Yamakawa et al. | |
| 2005/0142033 A1* | 6/2005 | Glezer | B01L 3/5085 422/400 |
| 2008/0191024 A1* | 8/2008 | Napper | G06F 3/03545 235/462.12 |
| 2010/0288056 A1 | 11/2010 | Clark et al. | |
| 2013/0082099 A1* | 4/2013 | Furrer | G01N 35/00732 235/375 |
| 2013/0129166 A1* | 5/2013 | Muller | B01D 21/262 382/128 |

* cited by examiner

SYSTEMS AND METHODS FOR READING MACHINE-READABLE LABELS ON SAMPLE RECEPTACLES

CROSS-REFERENCE TO RELATED APPLICATIONS AND INCORPORATION BY REFERENCE

The following application is a related application that is incorporated herein by reference in its entirety: U.S. Provisional Application No. 62/143,963, filed Apr. 7, 2015.

FIELD

Embodiments of this disclosure are directed to systems and methods for reading machine-readable labels on sample receptacles, for example, sample receptacles used to perform assays.

BACKGROUND

An analyzer system can perform assays on fluid sample material. For example, in the clinical laboratory context, the analyzer system can be configured to perform multi-step analytical processes (for example, a nucleic acid test (NAT) designed to detect microbe, such as a virus or a bacterium) that involve adding substances (e.g., fluids), such as samples, solid supports, buffers, oil, primers, polymerases, nucleotides, labels, probes, or other reaction fluids, to and/or removing substances from receptacles, agitating receptacles to mix the contents thereof, maintaining and/or altering the temperature of the contents of the receptacles, heating or chilling the contents of the receptacles, altering the concentration of one or more content components of the receptacles, separating or isolating constituent components of the contents of the receptacles, detecting an electromagnetic signal emission (for example, light) from the contents of the receptacles, deactivating or halting an on-going reaction, or any combination of two or more of such processes.

The analyzer system can be automated to perform the desired analytical process. Accordingly, the analyzer system can automatically identify the contents of a sample receptacle and the assay to perform. For example, the analyzer system can read labels, for example, a barcode, on the sample receptacle to identify the contents of the sample receptacle and the assay to perform.

BRIEF SUMMARY

In some embodiments, a method of reading machine-readable labels on sample receptacles includes moving, between a first position and a second position in a housing, a sample rack configured to hold a plurality of sample receptacles. Each sample receptacle has a machine-readable label. The method also includes measuring an absolute position of the sample rack as the sample rack moves between the first position and the second position, and acquiring an image of the machine-readable label of each sample receptacle of the plurality of sample receptacles as the sample rack moves from the first position to the second position. Further, the method includes decoding the acquired image of the machine-readable label of each sample receptacle of the plurality of sample receptacles. In some embodiments, the method also includes associating a decoded acquired image of the machine-readable label of each sample receptacle of the plurality of sample receptacles with the corresponding sample receptacle based on a measured absolute position of the sample rack when the image of the machine-readable label was acquired. The machine-readable label can be a barcode. In some embodiments, the barcode can be a one- or two-dimensional barcode. In some embodiments, the barcode contains information that associates a sample within the sample receptacle to a patient. Moving the sample rack can include manually moving the sample rack or automatically moving the sample rack. In some embodiments, the sample rack is moved at a high rate of speed. In some embodiments, the second position in the housing is a fully inserted position, and decoding the acquired image occurs after the sample rack is moved to the second position. In some embodiments, measuring the absolute position of the sample rack uses a reader, and acquiring an image of the machine-readable label uses the reader. In some embodiments, measuring the absolute position of the sample rack uses a reader, and acquiring an image of the machine-readable label uses a second reader separate from the first reader. In some embodiments, acquiring the image of the machine-readable label comprises using a reader.

In some embodiments, a method of reading machine-readable labels on sample receptacles includes moving, between a first position and a second position in a housing, a sample rack configured to hold a plurality of sample receptacles. Each sample receptacle has a machine-readable label. The method also includes activating a label reader when the sample rack is at each of a plurality of predetermined positions between the first position and the second position to read the machine-readable label of each sample receptacle of the plurality of sample receptacles as the sample rack moves from the first position to the second position. In some embodiments, the method also includes activating a light source when the sample rack is at each of the plurality of predetermined positions. In some embodiments, moving the sample rack comprises manually moving the sample rack. In some embodiments, moving the sample rack comprises automatically moving the sample rack. In some embodiments, method also includes measuring a position of the sample rack as the sample rack moves between the first position and the second position. Measuring the position of the sample rack can include using a sensor operably coupled to an indicator on the sample rack. The indicator can include at least one of the group consisting of: a recess, a protrusion, an optically reflective element, a magnetic element, and a capacitive element. The machine-readable label can be a one- or two-dimensional barcode. The machine-readable label can be a two-dimensional barcode that contains information that associates a sample within the sample receptacle to a patient.

In some embodiments, a method of reading machine-readable labels on sample receptacles includes moving, between a first position and a second position in a housing, a sample rack configured to hold a plurality of sample receptacles. Each sample receptacle has a machine-readable label. The method also includes measuring positions of the sample rack as the sample rack moves between the first position and the second position. Further, the method includes reading the machine-readable label of each sample receptacle of the plurality of sample receptacles as the sample rack moves from the first position to the second position. And the method includes decoding a read machine-readable label of each sample receptacle of the plurality of sample receptacles. The method also includes associating a decoded machine-readable label of each sample receptacle of the plurality of sample receptacles with the corresponding receptacle based on a measured position of the sample rack when the machine-readable label was read. In some embodiments, moving the sample rack includes manually moving the sample rack. In other embodiments, moving the sample rack includes automatically moving the sample rack. In some embodiments, the machine-readable label contains information that associates a sample within the sample receptacle to a patient. In some embodiments, the second position in the housing is a fully inserted position, and decoding the machine-readable label occurs after the sample rack is moved to the second position. In some embodiments, the machine-readable label is a barcode. In some embodiments, the barcode is a one- or two-dimensional barcode.

In some embodiments, a method for reading machine-readable labels on sample receptacles includes reading, at a first location, a machine-readable label of each sample receptacle of a plurality of sample receptacles with a first label reader. The plurality of sample receptacles are held by a sample rack having a rack-identifying machine-readable label. The method also includes moving the rack from the first location to a separate second location and sensing, at the second location, a rack identifier on the sample rack with a sensor separate from the first label reader. And the method includes associating a sensed rack identifier with a read machine-readable label of each sample receptacle of a plurality of sample receptacles. In some embodiments, the rack identifier is a machine-readable label, and the sensor is a second label reader. In some embodiments, the rack identifier is an RFID tag, and the sensor is an RFID reader. In some embodiments, the method also includes acquiring location data identifying the second location to which the sample rack was moved. In some embodiments, the machine-readable label of each sample receptacle of a plurality of sample receptacles is a two-dimensional barcode. The two-dimensional barcode can contain information that associates a sample within the sample receptacle to a patient. In some embodiments, the method also includes determining whether a time period during which the sample rack was moved from the first location to the separate second location exceeds a predetermined time period threshold. In some embodiments, reading the machine-readable label of each sample receptacle of a plurality of sample receptacles occurs while the sample rack is moved between a first position and a second position at the first location. In some embodiments, the method also includes measuring a position of the sample rack as the sample rack moves between the first position and the second position; acquiring an image of the machine-readable label of each sample receptacle of the plurality of sample receptacles as the sample rack moves from the first position to the second position; decoding the acquired image of the machine-readable label of each sample receptacle of the plurality of sample receptacles; and associating a decoded acquired image of the machine-readable label of each sample receptacle of the plurality of sample receptacles with the corresponding sample receptacle based on a measured position of the sample rack when the image of the machine-readable label was acquired.

In some embodiments, a method of reading machine-readable labels on sample receptacles includes moving, between a first position and a second position along a first lane in a housing, a first sample rack configured to hold a first plurality of sample receptacles each having a machine-readable label. The method also includes moving a camera to focus the camera at a point along the first lane, and reading the machine-readable label of each sample receptacle of the first plurality of sample receptacles of the first sample rack as the first sample rack moves from the first position to the second position. The method also includes moving, between a first position and a second position along a second first lane different than the first lane in the housing, a second sample rack configured to hold a second plurality of sample receptacles each having a machine-readable label. Further, the method includes moving the camera to focus the camera at a point along the second lane and reading the machine-readable label of each sample receptacle of the second plurality of sample receptacles of the second sample rack as the second sample rack moves from the first position to the second position. In some embodiments, the camera is a fixed focal length camera. In other embodiments, the camera is a variable focal length camera. In some embodiments, moving the first sample rack includes manually moving the first sample rack, and moving the second sample rack includes manually moving the second sample rack. In other embodiments, moving the first sample rack includes automatically moving the first sample rack, and moving the second sample rack includes automatically moving the second sample rack. In some embodiments, the method also includes activating a light source simultaneously with reading the machine-readable label of each sample receptacle of the first plurality of sample receptacles of the first sample rack as the first sample rack moves from the first position to the second position, and activating the light source simultaneously with reading the machine-readable label of each sample receptacle of the second plurality of sample receptacles of the second sample rack as the second sample rack moves from the first position to the second position. In some embodiments, the method includes reading a rack-identifying machine-readable label on each of the first and second sample racks. The machine-readable label can be a two-dimensional barcode that, in some embodiments, contains information that associates a sample within the sample receptacle to a patient.

In some embodiments, a system for reading machine-readable labels on sample receptacles includes a housing and a camera configured to acquire an image of a machine-readable label of each sample receptacle of a plurality of sample receptacles as a sample rack configured to hold the plurality of sample receptacles moves between a first position and a second position within the housing. The system also includes a processing and control unit configured to decode an acquired image of the machine-readable label of each sample receptacle of a plurality of sample receptacles. The processing and control unit is also configured to associate a decoded acquired image of the machine-readable label of each sample receptacle of the plurality of sample receptacles with the corresponding receptacle based on a measured absolute position of the sample rack when the image of the machine-readable label was acquired. In some embodiments, the system also includes position sensor configured to measure an absolute position of the sample rack. The position sensor is configured to measure the absolute position of the sample rack using a position indicator on the sample rack. The position sensor can be a plurality of optic read sensors, a plurality of magnetic read sensors, a plurality of capacitive read sensors, a plurality of gears, or a plurality of friction wheels. In some embodiments, the camera is configured to acquire an image of an optical encoder strip on the sample rack, and the processing and control unit is configured to decode an acquired image of the optical encoder strip to measure the absolute position of the sample rack and configured to associate a measured absolute position of the sample rack with an acquired image of the machine-readable label of each sample receptacle of a plurality of sample receptacles. In some embodiments, the system is configured such that the sample rack is manually moved between the first position and the second position. In some embodiments, the system is configured such that the sample rack is automatically moved between the first position and the second position. The camera can be a line scan camera or an area scan camera. The machine-readable label can be a two-dimensional barcode that, in some embodiments, contains information that associates a sample within the sample receptacle to a patient. The camera can be disposed within the housing or coupled to the housing. The processing and control unit can be disposed within the housing or coupled to the housing.

In some embodiments, a system for reading machine-readable labels on sample receptacles includes a housing and a label reader configured to read a machine-readable label of each sample receptacle of a plurality of sample receptacles held by a sample rack that moves between a first position and a second position within the housing. The system also includes a processing and control unit configured to activate the label reader when the sample rack is at each of a plurality of predetermined positions between the first position and the second position to read the machine-readable label of each sample receptacle of the plurality of sample receptacles as the sample rack moves from the first position to the second position. In some embodiments, the label reader is further configured to read a machine-readable rack identifier label on the sample rack. In some embodiments, the system also includes a sensor operatively coupled to an RFID tag on the sample rack. In some embodiments, the system also includes a sensor operatively coupled to a position indicator on the sample rack to determine a position of the sample rack between the first position and the second position. The position sensor can be a plurality of optic read sensors, a plurality of magnetic read sensors, a plurality of capacitive read sensors, a plurality of gears, or a plurality of friction wheels. The processing and control unit can be configured to activate a light source when the sample rack is at each of the plurality of predetermined positions. The system can be configured such that the sample rack is manually moved between the first position and the second position. The system can also be configured such that the sample rack is automatically moved between the first position and the second position. In some embodiments, the label reader is disposed within the housing or coupled to the housing. In some embodiments, the processing and control unit is disposed within the housing or coupled to the housing.

In some embodiments, a system for reading machine-readable labels on sample receptacles includes a sample rack having a rack identifier and configured to hold a plurality of sample receptacles, each having a machine-readable label. The system also includes a first location configured to receive the sample rack, and a sensor configured to read the rack identifier when the sample rack is at the first location. The system also includes a second location configured to receive the sample rack, and a first label reader, separate from the sensor, configured to read the machine-readable label of each sample receptacle of the plurality of sample receptacles when the rack is at the second location. In some embodiments, the rack identifier is a machine-readable label, and the sensor is a second label reader. In some embodiments, the rack identifier is an RFID tag, and the sensor is an RFID reader. In some embodiments, the machine-readable label is a two-dimensional barcode that, in some embodiments, contains information that associates a sample within the sample receptacle to a patient. The system can be configured such that the sample rack is manually moved between a first position and a second position when at the first location. The system can also be configured such that the sample rack is automatically moved between a first position and a second position when at the first location.

In some embodiments, a system for reading machine-readable labels on sample receptacles includes a housing and a sample rack configured to hold a plurality of sample receptacles, each having a two-dimensional machine-readable label and configured to move between a first position and a second position within the housing. The system also includes a reader configured to read the two-dimensional machine-readable label of each sample receptacle of the plurality of sample receptacles as the sample rack moves between the first position and the second position. The system also includes a processing and control unit configured to decode the read two-dimensional machine-readable label of each sample receptacle of the plurality of sample receptacles. The processing and control unit is also configured to associate the decoded two-dimensional machine-readable label of each sample receptacle of the plurality of sample receptacles with the corresponding receptacle based on a measured position of the sample rack when the two-dimensional machine-readable label was read. In some embodiments, the system is configured such that the sample rack is manually moved between the first position and the second position. In other embodiments, the system is configured such that the sample rack is automatically moved between the first position and the second position. In some embodiments, the reader is disposed within the housing or coupled to the housing. In some embodiments, the processing and control unit is disposed within the housing or coupled to the housing.

In some embodiments, a system for reading machine-readable labels on sample receptacles includes a housing defining at least a first lane and a second lane. Each lane is configured to receive a sample rack adapted to hold a plurality of sample receptacles, and each of the sample receptacles has a machine-readable label. The system also includes a camera configured to move to a first position that focuses the camera at a first position along the first lane and to a second position that focuses the camera at a second position along the second lane second lane. The camera is configured to acquire an image of the machine-readable label of each sample receptacle of a first plurality of sample receptacles of a first sample rack moving along the first lane. The camera is also configured to acquire an image of the machine-readable label of each sample receptacle of a second plurality of sample receptacles of a second sample rack moving along the second lane. In some embodiments, the camera is a fixed focal length camera. In other embodiments, the camera is a variable focal length camera. In some embodiments, the camera is configured to acquire images of the machine-readable label of each sample receptacle of a plurality of sample receptacles of sample racks being manually moved along the first lane and the second lane. In some embodiments, the camera is configured to acquire images of the machine-readable label of each sample receptacle of a plurality of sample receptacles of sample racks being automatically moved along the first lane and the second lane. In some embodiments, the machine-readable label is a two-dimensional barcode that, in some embodiments, contains information that associates a sample within the sample receptacle to a patient. In some embodiments, the camera comprises a CCD camera or a CMOS camera. In some embodiments, the system also includes a light source configured to illuminate the machine-readable label of each sample receptacle within the housing. In some embodiments, the system includes a moveable stage to which the camera and the light source are coupled. In some embodiments, the camera is configured to move along a lane parallel to the first and second lane. In some embodiments, the system also includes a mirror positioned along an optical path between the camera and the first position on the first lane and the second position on the second lane.

BRIEF DESCRIPTION OF THE DRAWINGS

The accompanying drawings, which are incorporated herein and form a part of the specification, illustrate the embodiments and, together with the description, further serve to explain the principles of the embodiments and to enable a person skilled in the relevant art(s) to make and use the embodiments.

Figure 1:
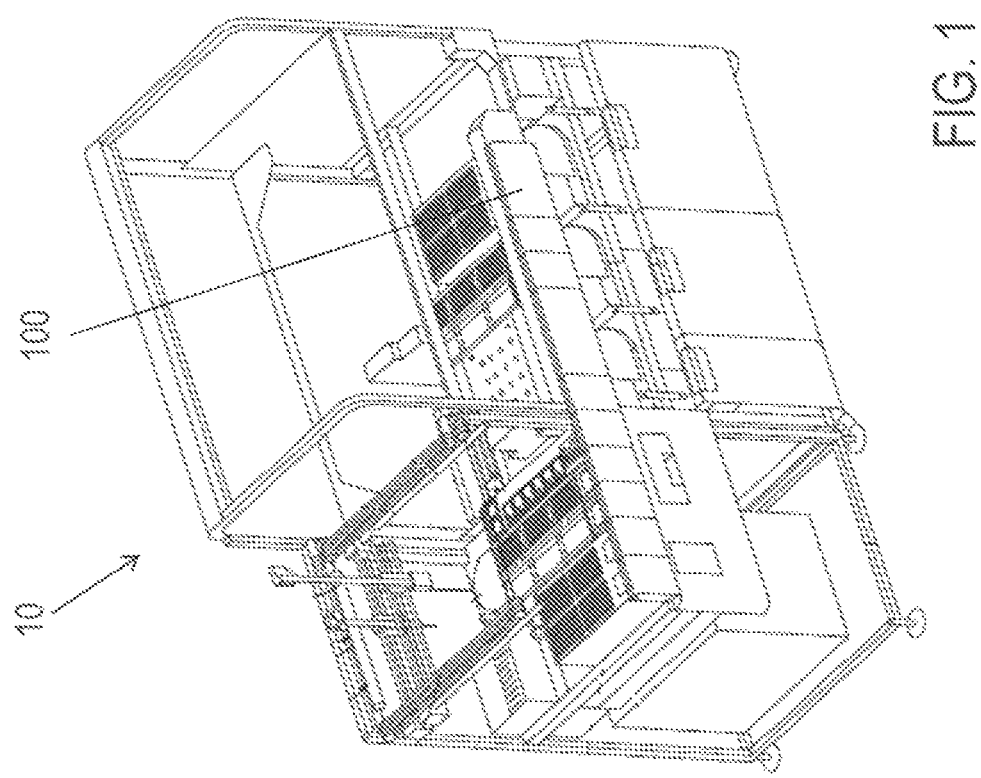
FIG. 1 illustrates a partial, perspective view of an analyzer system that includes a sample bay according to an embodiment.

The features and advantages of the embodiments will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

The present invention will now be described in detail with reference to embodiments thereof as illustrated in the accompanying drawings. References to "one embodiment," "an embodiment," "some embodiments," "an exemplary embodiment," "for example," "an example," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Some embodiments described in this application provide systems and methods for reading one- and two-dimensional barcodes on sample receptacles in applications in which there are one or more of the following design considerations: limited working space, strict field of view requirement, high resolution requirement, and high speed requirement (for example, when receptacles are manually moved by a user). For example, a system can include a housing (for example, a sample bay housing) configured to receive a plurality of sample racks along a plurality of lanes. Each sample rack holds sample receptacles having two-dimensional barcodes. The system includes a reader, for example, a laser barcode scanner or a camera, that reads the two-dimensional barcode. The system also includes a processing and control unit that decodes the read two-dimensional barcodes to obtain information from the barcodes and associate the information with a corresponding sample receptacle. Such systems and methods for reading two-dimensional barcodes on sample receptacles can be used for performing assays on fluid sample material and for identifying the contents of the sample receptacles, for example, patient information (e.g., patient identification numbers).

Figure 2:
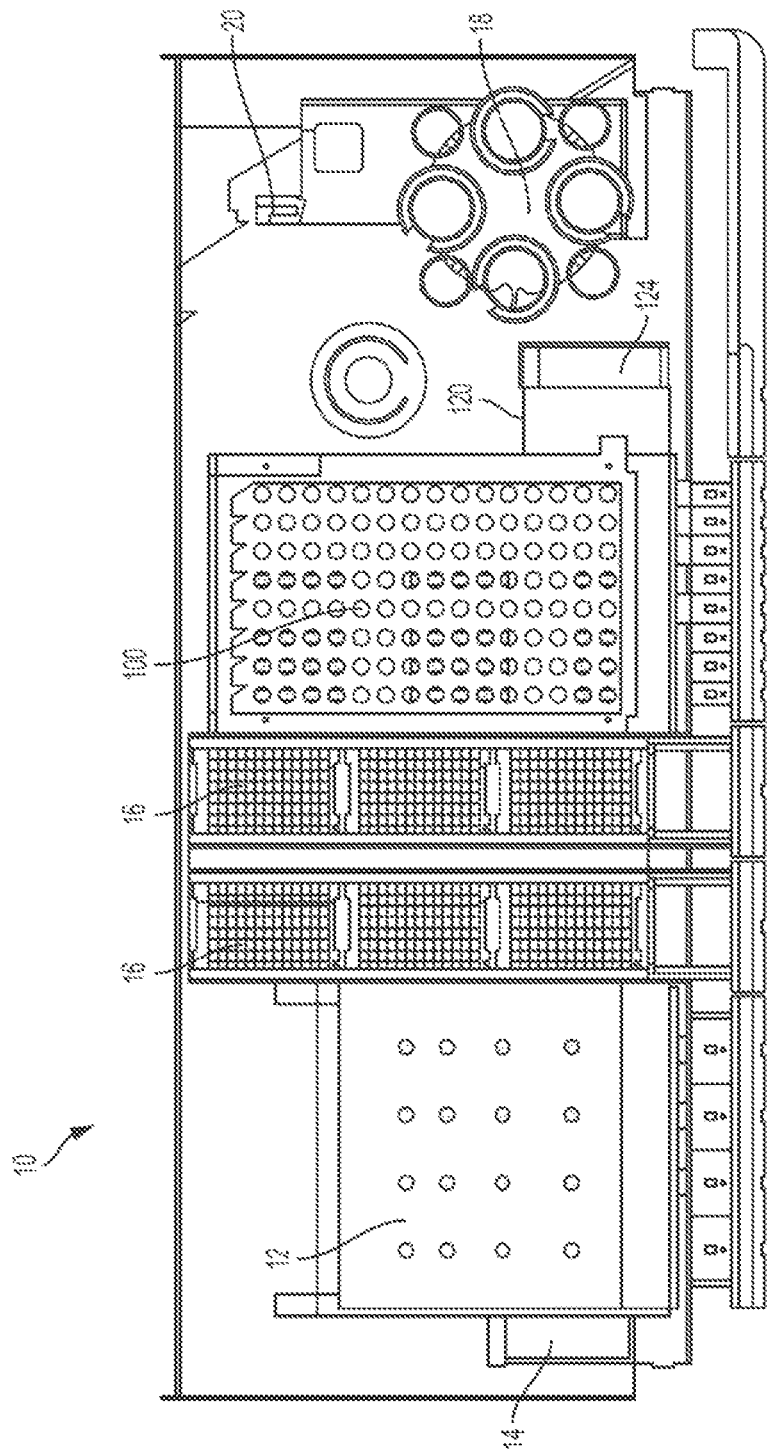
FIG. 2 illustrates a cross-sectional plan view of the analyzer system of FIG. 1 according to an embodiment.

FIGS. 1 and 2 illustrate perspective and plan views, respectively, of an exemplary analyzer system 10 for performing assays on fluid sample material. In some embodiments, analyzer system 10 is configured to perform a multistep analytical process (for example, a nucleic acid test (NAT) designed to detect microbe, such as a virus or a bacterium) or other chemical, biochemical or biological processes. Exemplary process steps include, for example, adding substances (e.g., fluids), such as samples, solid supports, buffers, oil, primers, polymerases, nucleotides, labels, probes, or other reaction fluids, to and/or removing substances from receptacles, agitating receptacles to mix the contents thereof, maintaining and/or altering the temperature of the contents of the receptacles (for example, using heated incubators configured to receive a plurality of reaction receptacles and maintain the receptacles in an elevated temperature environment), heating or chilling the contents of the receptacles (for example, using temperature ramping stations configured raise the temperature of the contents of reaction receptacles or chilling modules configured to reduce the temperature of the contents of the receptacles), altering the concentration of one or more content components of the receptacles, separating or isolating constituent components of the contents of the receptacles (for example, using magnetic separation wash stations configured to isolate a target nucleic acid immobilized on a magnetically-responsive solid support from the contents of the receptacle), detecting an electromagnetic signal emission (for example, light) from the contents of the receptacles (for example, using detector configured to detect a signal (e.g., an optical signal) emitted by the contents of the reaction receptacle), deactivating or halting an on-going reaction, or any combination of two or more of such processes. Fluid sample material may include, for example, urine, blood, plasma, sputum, saliva, mucus, pus, seminal fluid, amniotic fluid, cerebrospinal fluid, synovial fluid, and cultures.

In some embodiments, fluid sample material is introduced into analyzer system 10 via a sample bay 100. FIG. 2 illustrates a cross-sectional view of analyzer 10 according to an embodiment. As shown in FIG. 2, analyzer 10 includes a sample bay 100 configured to receive a plurality of sample racks, which is described further below. In some embodiments, analyzer 10 also includes a reagent bay 12. Reagent bay 12 is configured to store one or more containers of reagents used during a multi-step analytical process. In some embodiments, analyzer 10 includes a reader 14, for example, a barcode reader, configured to read machine-readable labels, for example, barcodes, on the reagent containers stored within reagent bay 12. In some embodiments, analyzer 10 includes one or more tip drawers 16 configured to store a plurality of tips used by a fluid transfer device. In some embodiments, analyzer 10 includes a target capture reagent carousel 18 configured to support and rotate one or more containers of a target capture reagent (TCR). In some embodiments, analyzer 10 includes a reader 20, for example, a barcode reader, configured to read machine-readable labels, for example, barcodes, on TCR containers on TCR carousel 18.

Figure 3:
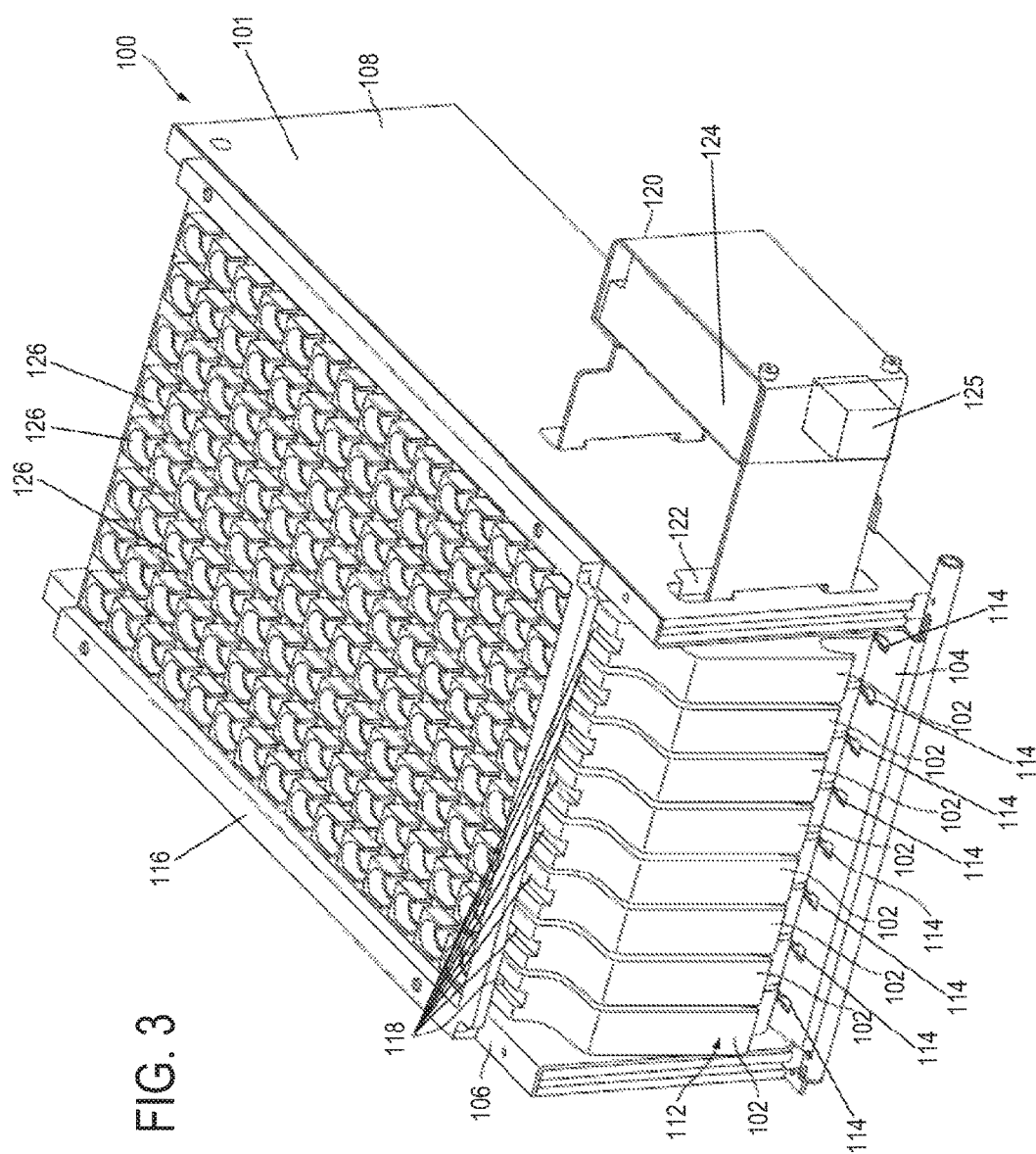
FIG. 3 illustrates a front perspective view of a sample bay according to an embodiment.
Figure 4:
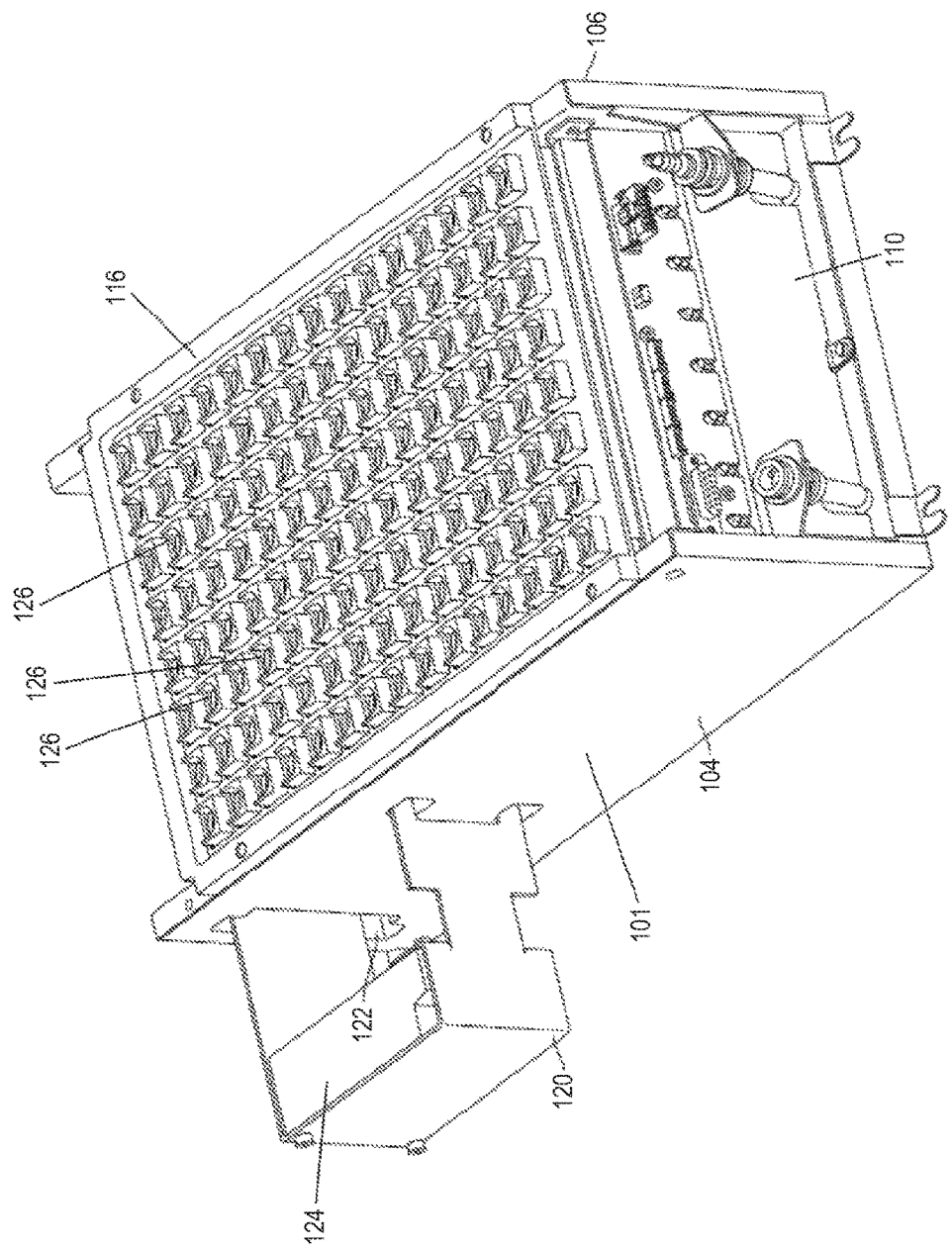
FIG. 4 illustrates a rear perspective view of the sample bay of FIG. 3 according to an embodiment.

FIGS. 3 and 4 illustrate front and rear perspective views, respectively, of a sample bay 100 according to an embodiment. Sample bay 100 is configured to receive a plurality of sample racks 102 along defined lanes within sample bay 100. Sample racks 102 support a plurality of sample receptacles (not shown in FIGS. 3 and 4) that contain fluid sample material. For example, as shown in FIG. 3, sample bay 100 is configured to receive eight sample racks 102 that move along defined lanes within sample bay 100. In other embodiments, sample bay 100 is configured to receive less than or more than eight sample racks 102.

Referring to FIGS. 3 and 4, sample bay 100 includes a housing 101 that defines an interior compartment that receives sample racks 102. Housing 101 can be rectangular as shown FIGS. 3 and 4 or any other suitable shape. In some embodiments, housing 101 includes a base 104 that is planar and rectangular, a first sidewall 106 and a second sidewall 108 extending from opposing sides of base 104, and a back wall 110 extending from a back side of base 104 between first and second sidewalls 106 and 108. Housing 101 has an opening 112 at its front end to allow sample racks 102 to be inserted into and removed from the compartment defined by housing 101.

In some embodiments, housing 101 defines a plurality of lanes along which sample racks 102 move, for example, eight lanes as shown in FIGS. 3 and 4. In some embodiments, base 104 includes a plurality of guides 114 that define the lanes of housing 101. Guides 114 are protrusions that extend from base 104 and are configured to operatively mate with a corresponding recess of sample racks 102. Guides 114 can help ensure that sample racks 102 are accurately and repeatably positioned in the defined lanes of housing 101 as sample racks 102 move. As shown in FIGS. 3 and 4, the lanes are straight and extend from the front end of housing 101 to the back end of housing 101.

In some embodiments, housing 101 also includes a top panel 116. In some embodiments, top panel 116 includes a plurality of guides 118 that define, along with guides 114, the lanes in which sample racks 102 move. Guides 118 can be protrusions that extend from top panel 116 toward base 104 and that are configured to operatively mate with corresponding recesses on sample racks 102. In some embodiments, top panel 116 defines a plurality of sample receptacle access openings 126, which in some embodiments as shown in FIG. 3, are arranged in a rectangular array of rows and columns. Each column of openings 126 is aligned with a respective sample rack 102, providing the system, for example, an analyzer system, with easy access to receptacles held by sample racks 102.

Sample bay 100 also includes a reader 124 configured to read machine-readable labels on sample racks 102, including machine-readable labels on receptacles held by sample racks 102. In some embodiments, as shown in FIGS. 3 and 4, sample bay 100 includes a reader support 120 configured to support reader 124. In some embodiments, reader 124 is coupled to reader support 120 and, thus, coupled to housing 101. As shown in FIGS. 3 and 4, reader support 120 is fixedly coupled to housing 101, for example, fixedly coupled to side wall 108. In some embodiments, when viewed from above, reader support 120 is U-shaped and forms a compartment sized to receive and support reader 124. And reader 124 is coupled to reader support 120, fixing the position of reader 124 relative to housing 101 in some embodiments.

Side wall 108 defines an opening 122 extending into the interior compartment defined by housing 101 such that reader 124 can read labels on sample racks 102 within housing 101 through opening 122. In some embodiments, reader 124 is configured to read machine-readable labels as sample racks 102 are pushed into or removed from housing 101 or after sample racks 102 are fully inserted into housing 101. In some embodiments, reader 124 is configured to read, for example, barcodes. In some embodiments, reading machine-readable labels comprises emitting light from a light source and measuring the intensity of light reflected back from the machine-readable label as the light source scans across the machine-readable label, for example, by using a laser barcode reader. In other embodiments, reading machine-readable labels comprises acquiring an image of the machine-readable label. In some embodiments, reader 124 is configured to read two-dimensional barcode labels (and in some embodiments, one-dimensional barcode labels or both one- and two-dimensional barcode labels) on sample racks 102, including machine-readable labels on receptacles held by sample racks 102.

In some embodiments, reader 124 is disposed outside of housing 101 and spaced was from opening 122 as shown in FIGS. 3, 4, and 11-16. In some embodiments (not shown), reader 124 is disposed outside of housing 101 and directly adjacent opening 122. In other embodiments (not shown), reader 124 is disposed within housing 101.

In some embodiments, as shown in FIG. 3, sample bay 100 includes a light source 125, for example, a strobe light, configured to illuminate the interior of housing 101. For example, light source 125 can illuminate labels on sample receptacles 128 within housing 101. As shown in FIG. 3, for example, light source 125 is near reader 124 and coupled to reader support 120. In some embodiments, light source 125 includes an array of LEDs. In some embodiments (not shown), light source 125 is disposed inside housing 101 or any other suitable location. In some embodiments, light source 125 is embodied within reader 124.

In some embodiments, sample bay 100, including reader 124 and its data processing system, are configured as described in the various embodiments disclosed in International Application No. PCT/US2010/035146, filed on May 17, 2010, and in U.S. Patent Application Publication No. 2012/0261469, published on Oct. 18, 2012, both of which are incorporated by reference in this application.

Figure 5:
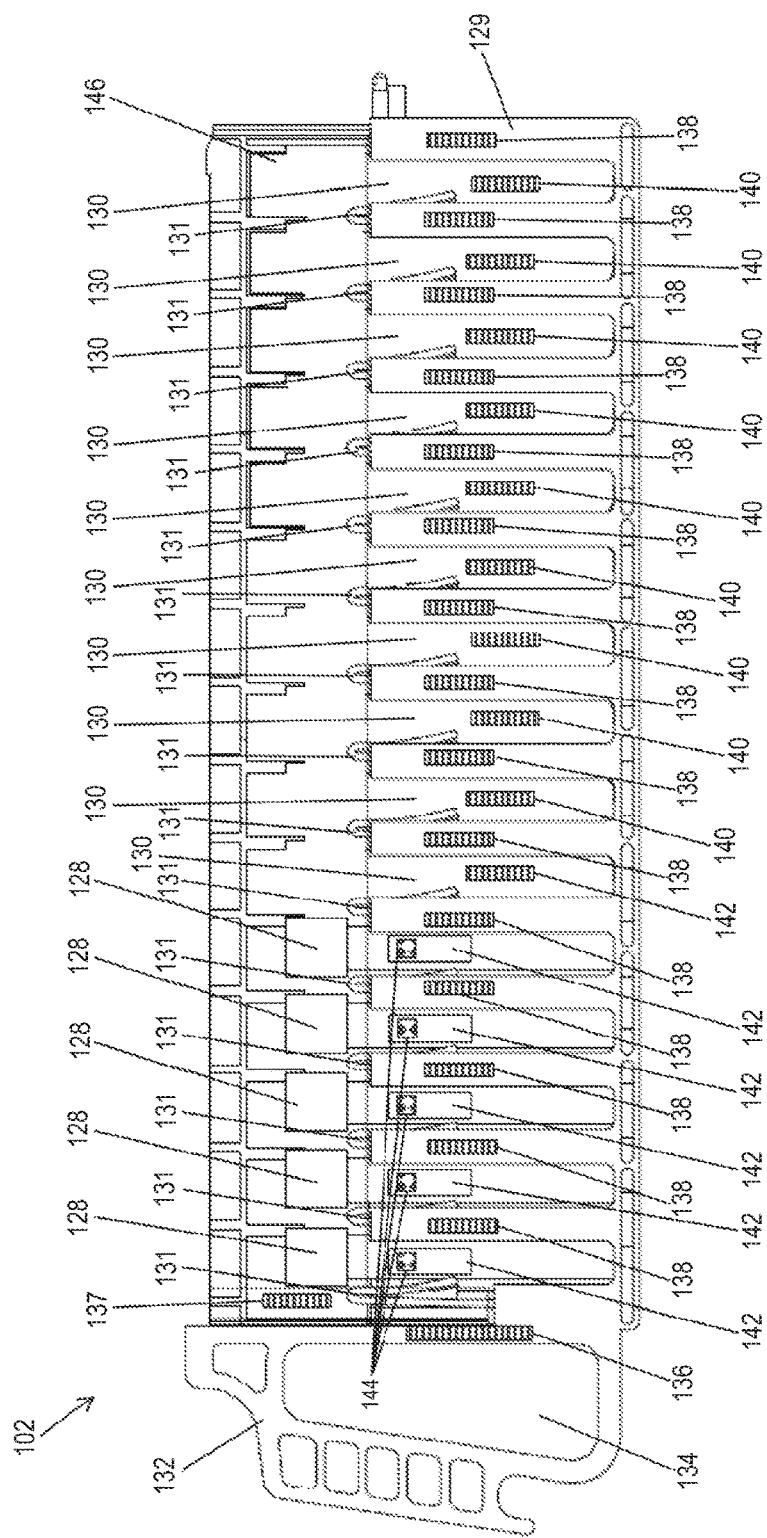
FIG. 5 illustrates a sample rack configured to hold a plurality of sample receptacles with a portion of a cover removed for illustrative purposes according to an embodiment.

FIGS. 5-10 illustrate various embodiments of sample rack 102. Referring to FIG. 5, sample rack 102 is configured to hold a plurality of sample receptacles 128. For example, as shown in FIG. 5, sample rack 102 is configured to hold 15 sample receptacles 128. In some embodiments, sample rack 102 includes a base 129 that defines a plurality of pockets 130 for closely receiving sample receptacles 128. Pockets 130 can be separated from each other by a vertical dividing wall in some embodiments. In some embodiments, sample receptacles 128 are tubular containers, for example, test tubes. In other embodiments, sample receptacles 128 can be any other container suitable for holding a fluid or liquid, for example, a cuvette, beaker, or microtiter plate. In some embodiments, as shown in FIG. 5, sample receptacles 128 include a cap that seals sample receptacles 128. The cap can be penetrated by the probe of a fluid transfer mechanism of analyzer system 10. In some embodiments, sample rack 102 is made from a suitable, non-reactive material, for example, plastic or Delrin® acetyl resin.

Figure 6:
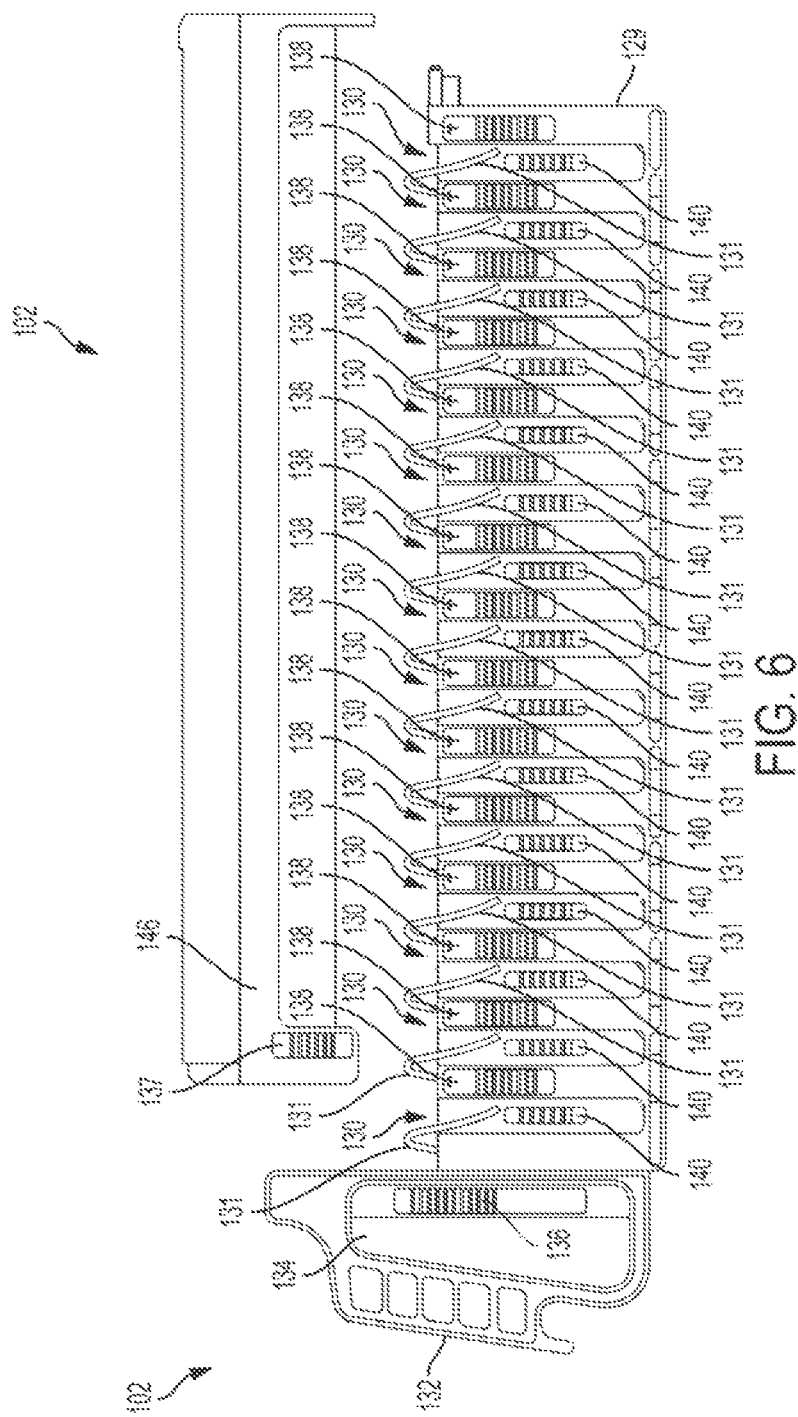
FIG. 6 illustrates a side view of a sample rack with a cover uncoupled from a base of the sample rack according to an embodiment.

In some embodiments, as best seen in FIGS. 5 and 6, sample rack 102 includes a resilient element, such as a spring clip 131, for each pocket 130. Spring clip 131 comprises a bent element (made of, e.g., spring stainless steel) with one portion attached to a dividing wall defining pocket 130 and another portion extending at an acute angle into pocket 130. Each spring clip 131 can accommodate sample receptacles 128 of varying sizes. A sample receptacle 128 is held in a relatively secure, fixed position within pocket 130 by means of spring clip 131 which urges sample receptacle 128 toward a dividing wall forming one side of pocket 130.

As shown in FIG. 5, sample rack 102 includes a handle 132 configured to allow a user to grasp and manually move sample rack 102 in some embodiments. For example, a user can grasp handle 132 to insert or remove sample rack 102 from housing 101 of sample bay 100. In some embodiments, handle 132 defines an opening 134 that is configured to allow a user's fingers to pass through. And in some embodiments, opening 134 allows the optical path 150 (see FIGS. 11 and 12) of reader 124 to pass through sample rack 102 to read a machine-readable label on a sample rack 102 positioned on the other side of opening 134 from reader 124.

In some embodiments, sample rack 102 includes a rack identifier 136 that provides unique rack-identifying information, for example, a rack identification number. In some embodiments (not shown), rack identifier 136 is an RFID tag. In such RFID embodiments, sample bay 100 includes an RFID reader configured to interrogate the RFID tag when sample rack 102 is within sample bay 100. In other embodiments, rack identifier 136 is a machine readable label, for example, a one- (as shown in FIG. 5) or two-dimensional barcode. In such machine-readable-label embodiments, reader 124 is a label reader configured to read rack identifier 136. Rack identifier 136 can be positioned near handle 132 of sample rack 102, as shown in FIG. 5.

In some embodiments, sample rack 102 includes a pocket identifier 138, for example, a one- (as shown in FIG. 5) or two-dimensional barcode that provides unique pocket identifying information for each pocket 130 of sample rack 102. In some embodiments, pocket identifier 138 indicates the position of a corresponding pocket 130 on sample rack 102 and, thus, the position of a sample receptacle 128 in the corresponding pocket 130 on sample rack 102. In some embodiments, pocket identifiers 138 are located on the outer surface of dividing walls that separate adjacent pockets 130 from each other. In some embodiments, pocket identifier 138 includes an alphanumeric identifier, for example, "A," "B," "C," etc., that uniquely identifies each pocket 130. In some embodiments, sample rack 102 includes an empty-recess identifier 140, for example, a machine-readable label such as a one- (as shown in FIG. 5) or two-dimensional barcode, that is used to identify pockets 130 that do not contain a sample receptacle 128. For example, as shown in FIG. 5, empty-recess identifier 140 is located within each pocket 130.

In some embodiments, sample rack 102 also includes a cover 146 configured to fit over the top of sample receptacles 128 held within pockets 130 of sample rack 102. In some embodiments, cover 146 is transparent or translucent such that the contents of pockets 130 can be observed without removing cover 146. Cover 146 is configured to be releasably secured to base 129 of sample rack 102. In other embodiments, sample rack 102 does not include a cover 146.

Referring to FIGS. 5 and 6, cover 146 includes a machine-readable label 137 such as a one- (as shown in FIG. 5) or two-dimensional barcode. Label 137 is configured to be used to determine whether cover 146 is coupled to base 129 and/or positioned properly relative to base 129.

As shown in FIG. 5, each sample receptacle 128 within sample rack 102 includes a label 142 in some embodiments. In some embodiments, labels 142 include machine-readable labels 144, for example, one- or two-dimensional (as shown in FIG. 5) barcodes. Two-dimensional barcodes express information in two directions, for example, in the horizontal and vertical directions, and include stacked barcodes and matrix barcodes. Two-dimensional barcodes include, for example, Aztec codes, PDF417 codes, MaxiCodes, Codablock codes, Data Matrix codes, and QR codes. Two-dimensional barcodes can improve decoding accuracy and increase the amount of information contained within the barcode relative to a one-dimensional barcode. In some embodiments, two-dimensional barcode labels 144 contain one or more of the following items of information: patient information such as a unique patient identifier (for example, patient name or patient identification number), patient metadata (for example, date of birth, age, sex, height, or weight), medical history, or any other desired patient information; and sample information such as the healthcare provider requesting the assay, the date the sample was collected, the collection site, the type of assays to be performed, assay test results, and other suitable information.

In some embodiments, two-dimensional barcode labels 144 have features as small as 0.2 mm×0.2 mm. In such embodiments, reader 124 is configured to accurately read two-dimensional barcode labels 144 when sample rack 102 is moving at high speeds, for example, speeds greater than 100 mm/sec, for example, speeds greater than 300 mm/sec, 500 mm/sec, 600 mm/sec, and 1000 mm/sec.

Figure 7:
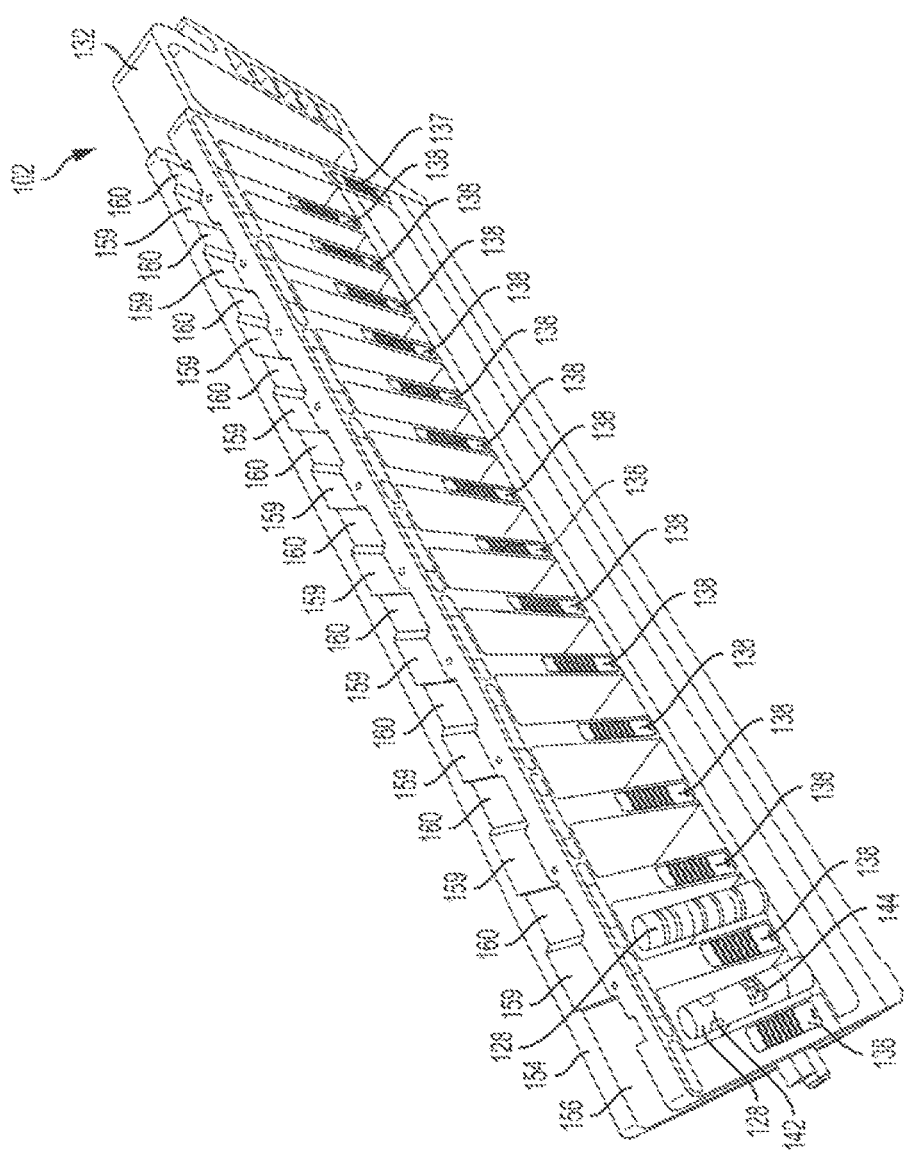
FIG. 7 illustrates bottom perspective view of a sample rack according to an embodiment.

Referring to FIG. 7, which illustrates a bottom surface 154 of sample rack 102, sample rack 102 includes a recessed guide track 156 configured to operatively mate with guides 114 on base 104 of housing 101 in some embodiments. For example, a bottom surface 154 of sample rack 102 can form recessed guide track 156 that engages sample rack guides 114 to ensure proper and repeatable positioning of sample racks 102 along the defined lanes in housing 101. Although spring clips 131 are not illustrated in FIG. 7, sample rack 102 in FIG. 7 can include spring clips 131.

In some embodiments, sample bay 100 is configured such that sample racks 102 are manually inserted within housing 101 of sample bay 100. In this application, "manually inserted," "manually moved," or similar phrases mean that sample racks 102 are inserted or moved without using automated or electrical device components. That is, sample racks 102 are inserted or moved within housing 101 along the defined lanes using only the user's hands. When sample racks 102 are manually moved, sample racks 102 can move at a high speed that exceeds 100 mm/sec, for example, speeds greater than 300 mm/sec, 500 mm/sec, 600 mm/sec, or 1000 mm/sec.

In other embodiments, sample bay 100 is configured to automatically move sample rack 102 within housing 101 of sample bay 100. For example, sample bay 100 can include an automated actuator that moves sample racks 102 within housing 101 of sample bay 100 to a fully inserted position. In some embodiments, sample rack 102 is automatically moved within housing 101 at a known, constant speed.

Figure 11:
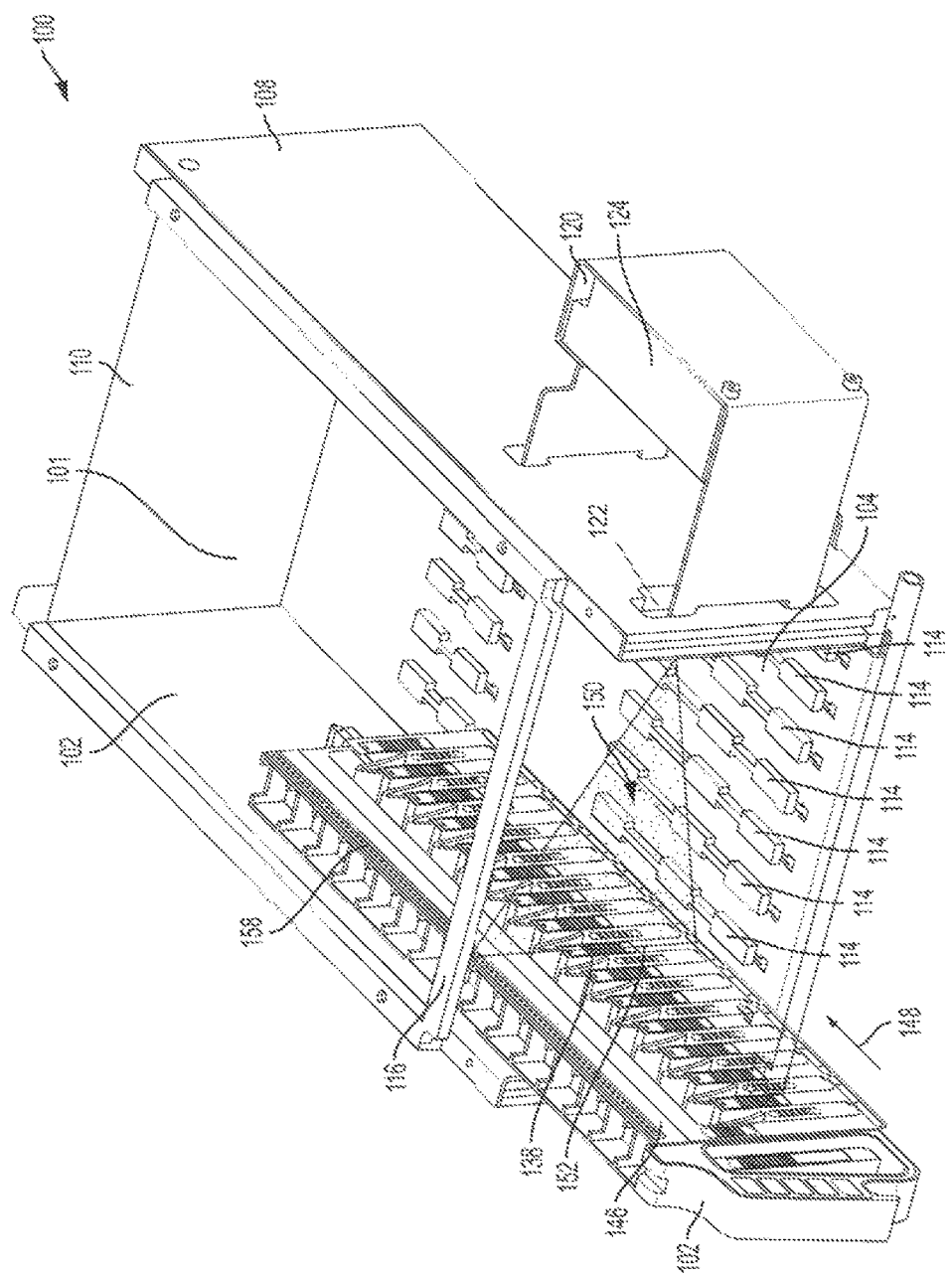
FIG. 11 illustrates a front perspective view of a sample bay with a rack partially inserted into a housing of the sample bay according to an embodiment.

To place a sample rack 102 within housing 101 of sample bay 100, a user aligns guide track 156 with guides 114 on base 104. The user then moves sample rack 102 in a direction 148 (as shown in FIG. 11) along a lane defined by guides 114 from a first, initial position to a second, fully inserted position within housing 101 of sample bay 100. In some embodiments, sample bay 100 includes sensors that detect the presence of sample rack 102 and whether sample rack 102 is fully inserted into the sample bay 100. As best seen in FIG. 5, sample receptacles 128 are placed in sample rack 102 such that labels 142 are aligned with the openings defined by the dividing walls that separate adjacent pockets 130 from each other. Accordingly, labels 142 are visible to reader 124 through opening 122 defined in side wall 108 of housing 101. Thus, as sample rack 102 moves from the initial position to the fully insert, reader 124 can read labels 142 on each sample receptacle 128 on sample rack 102.

In some embodiments, sample bay 100 includes a position measurement system that measures the position of sample rack 102 within housing 101. In some embodiments, the position measurement system is configured to determine the absolute position of sample rack 102. In this application, "absolute position" means the exact position of sample rack 102 within sample bay 100. In contrast, for example, "incremental position" means an incremental range of positions that sample rack 102 could be within sample bay 100 from a reference point.

Figure 8:
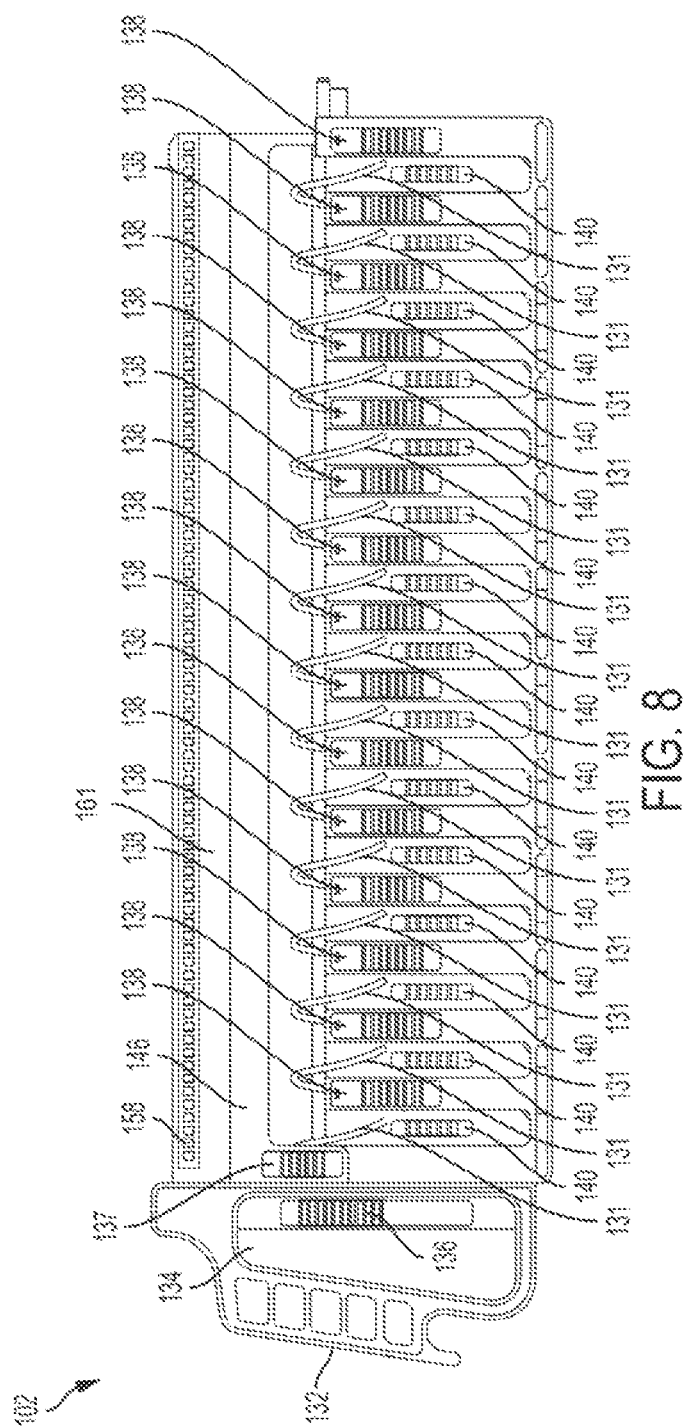
FIG. 8 illustrates a side view of a sample rack having a position indicator according to an embodiment.
Figure 9:
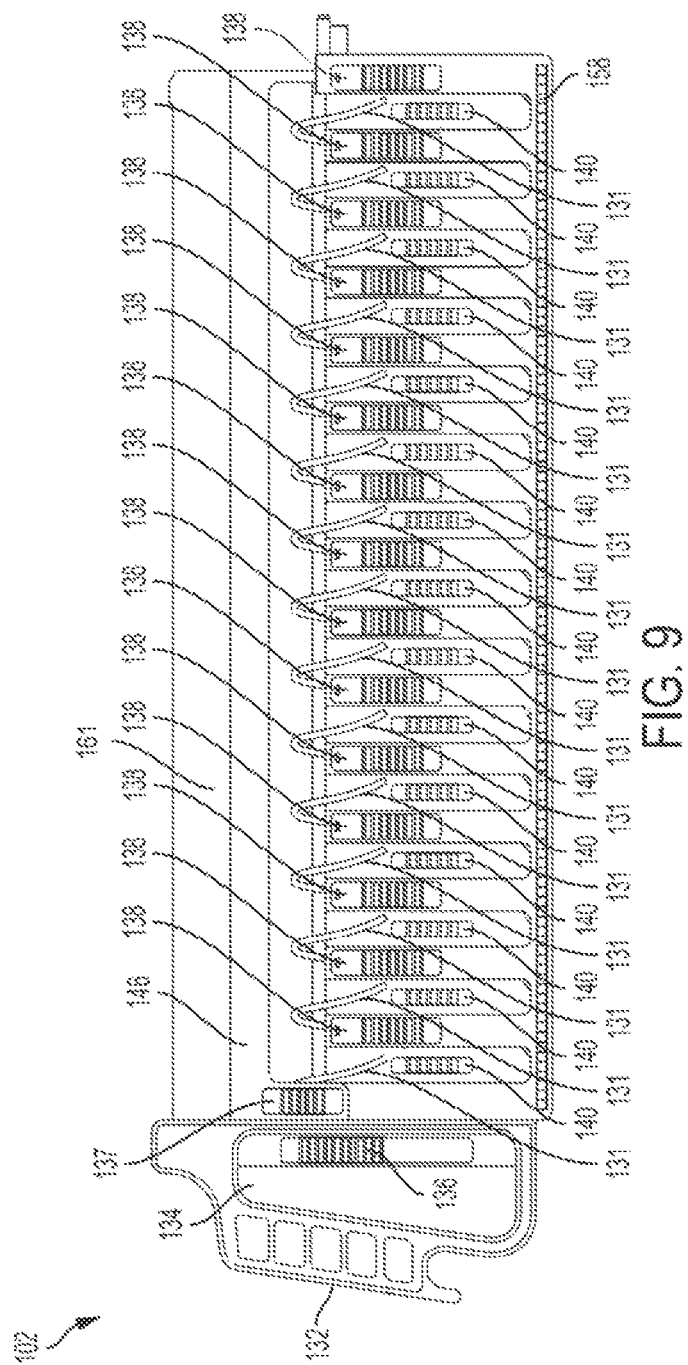
FIG. 9 illustrates a side view of a sample rack having a position indicator according to another embodiment.
Figure 10:
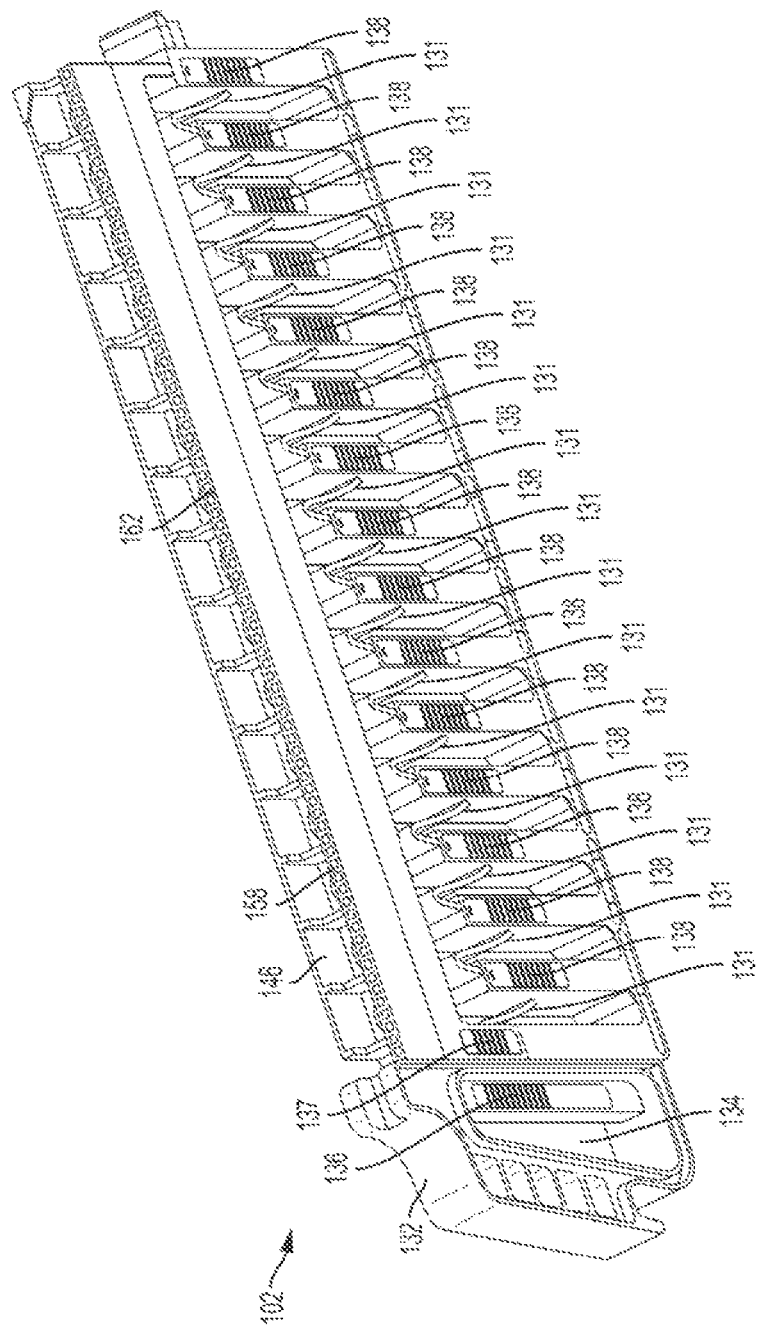
FIG. 10 illustrates a rear perspective view of a sample rack having a position indicator according to yet another embodiment.

In some embodiments, in which sample bay 100 includes an absolute position measurement system, sample rack 102 includes an absolute position indicator 158. In some embodiments, position indicator 158 extends along a length of sample rack 102 (for example, along base 129 or cover 146) that overlaps with pockets 130. For example, referring to FIGS. 8 and 10, position indicator 158 extends along a length of cover 146 that overlaps all pockets 130 defined in sample rack 102 in some embodiments. In FIG. 8, position indicator 158 is located on a side surface 161 of cover 146, and in FIG. 10, position indicator 158 is positioned on a top surface 162 of cover 146. In some embodiments, position indicator 158 extends along a length of base 129 that overlaps all pockets 130 defined in sample rack 102. And referring to FIG. 7, in some embodiments, position indicator 158 is positioned on a bottom surface 154 of sample rack 102. In some embodiments, structural features of sample rack 102 form position indicator 158. For example, in FIG. 7, guide track 156 also functions as position indicator 158. Guide track 156 includes a repeating, alternating pattern of offset sections 159 and 160. Position indicator 158 can be positioned at any other suitable locations.

In some embodiments, position indicator 158 can be an optical encoder strip affixed to sample rack 102, a magnetic encoder strip affixed to sample rack 102, a friction strip formed on sample rack 102, or a plurality of recesses in a repeating pattern (including, for example, through-holes) formed on sample rack 102, or a plurality of protrusions in a repeating pattern (including, for example, gear teeth) formed on sample rack 102.

Figure 13:
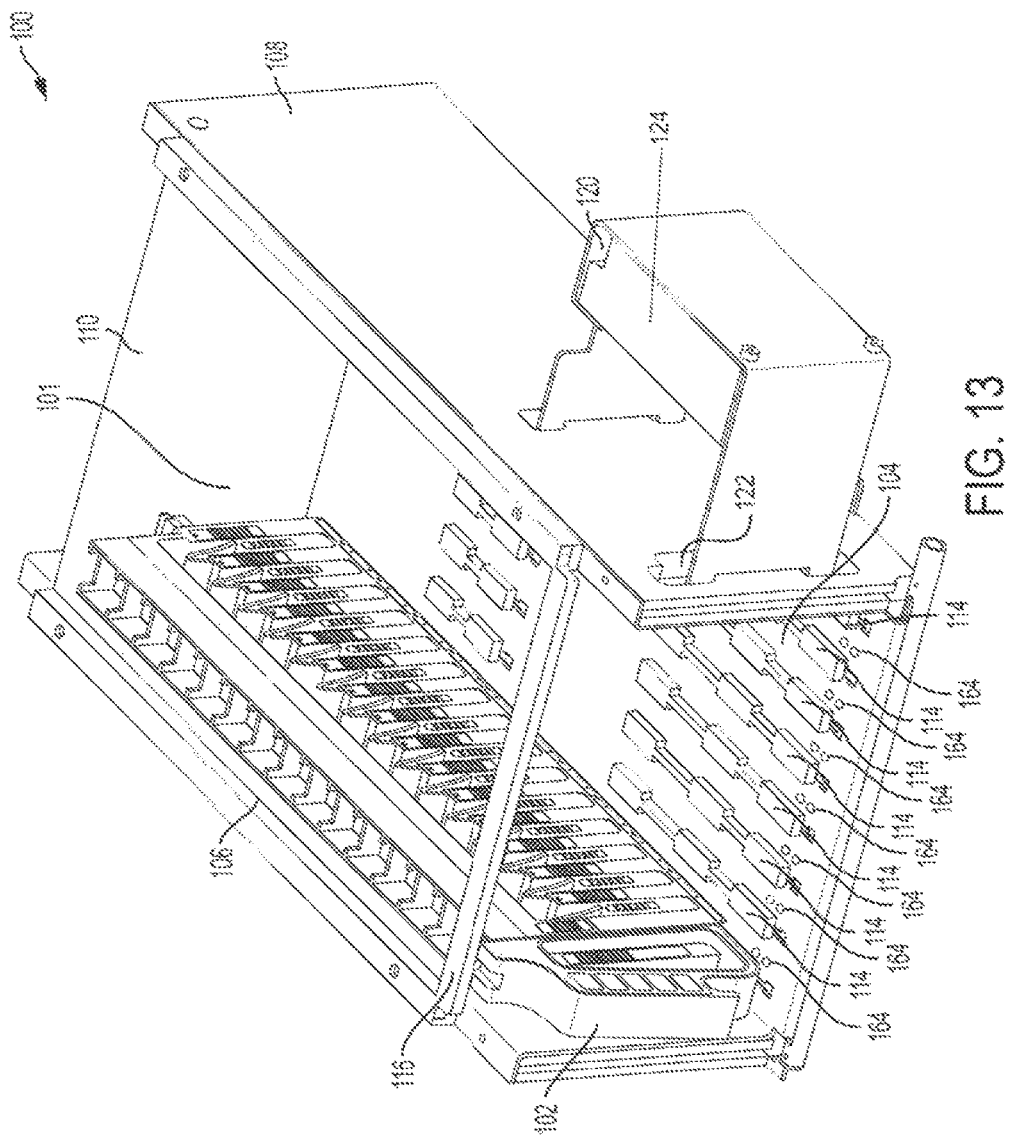
FIG. 13 illustrates a front perspective view of the sample bay having position sensors according to an embodiment.
Figure 14:
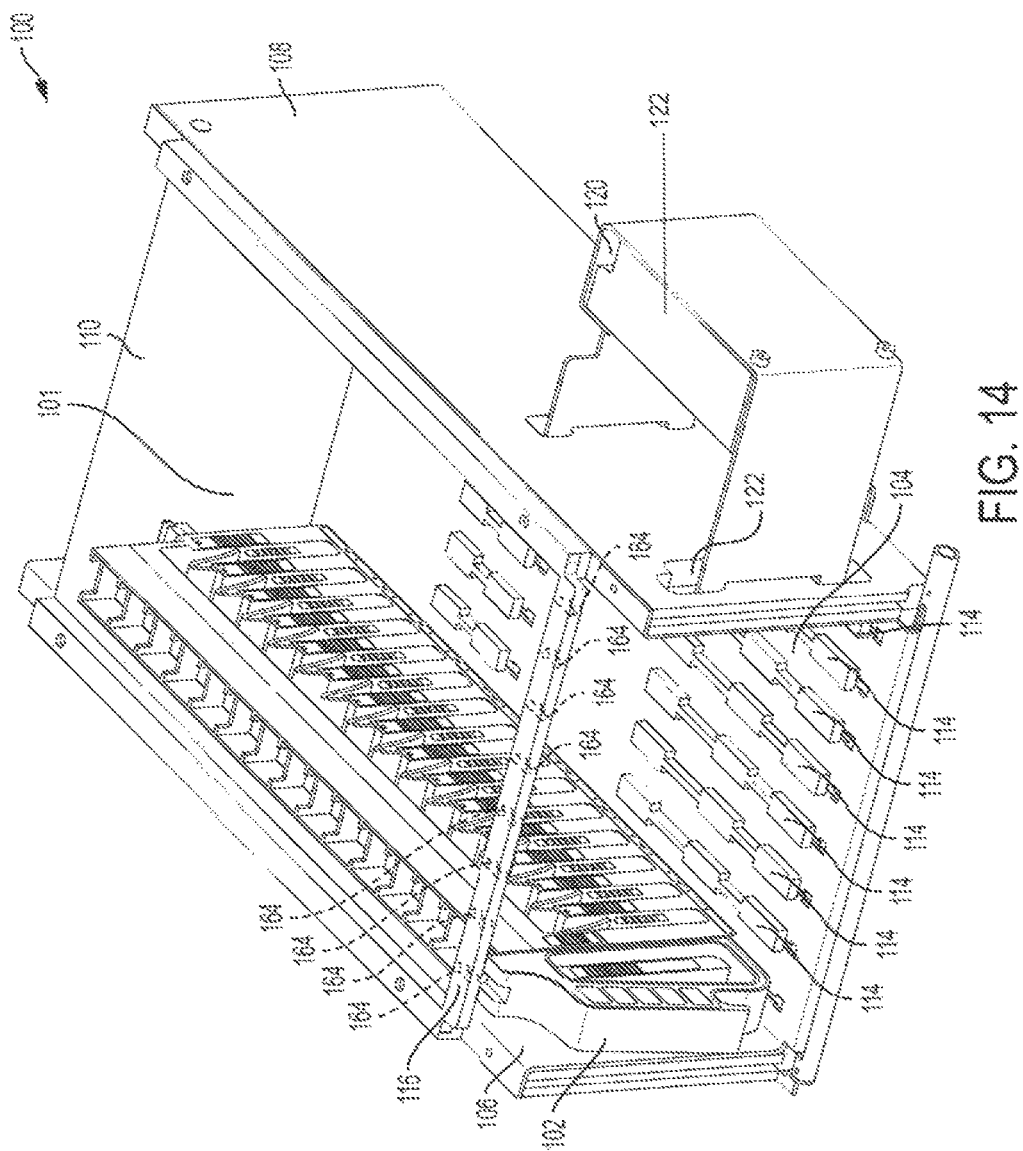
FIG. 14 illustrates a front perspective view of the sample bay having position sensors according to another embodiment.
Figure 15:
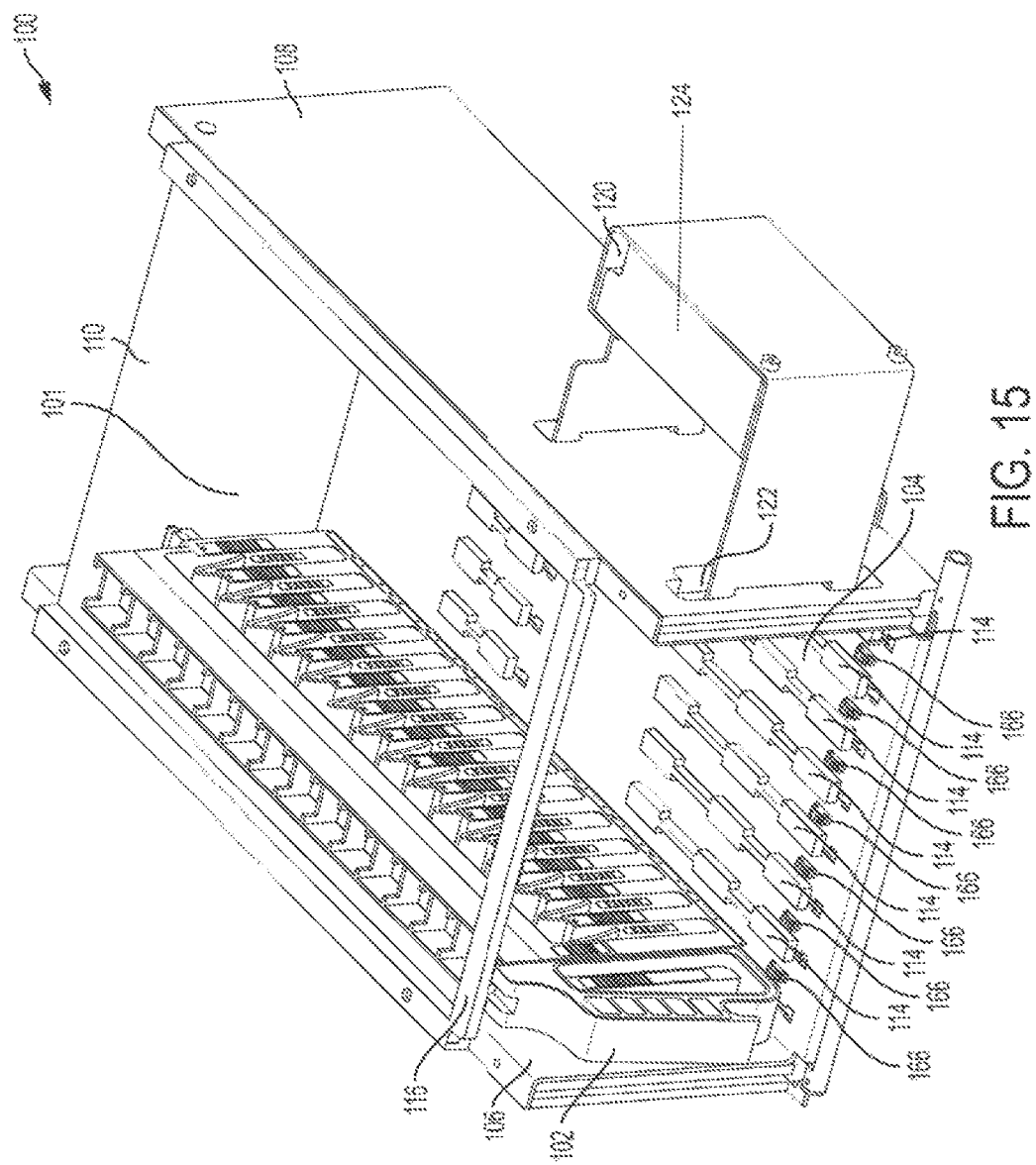
FIG. 15 illustrates a front perspective view of the sample bay module having position sensors according to yet another embodiment.
Figure 16:
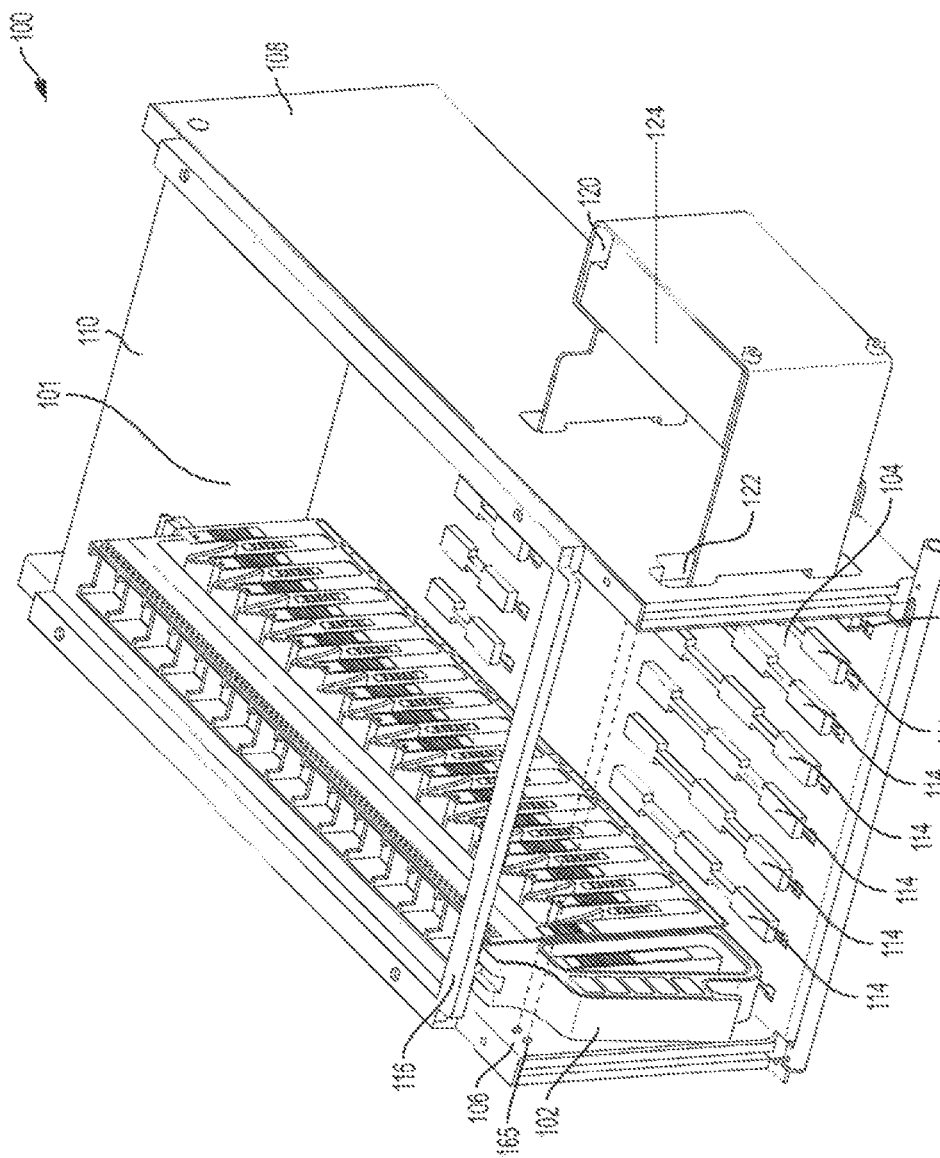
FIG. 16 illustrates a front perspective view of the sample bay having position sensors according to another embodiment.

In some embodiments, the position measurement system includes a position sensor that operatively corresponds to the type of position indicator 158 coupled to sample rack 102. For example, in some embodiments in which positioning indicator 158 is an optical encoder strip or a magnetic encoder strip affixed to sample rack 102, the measurement system can include optical or magnetic read sensors 164 coupled to housing 101 and configured to read the optical encoder strip or the magnetic encoder strip as sample rack 102 passes near (for example, over, under, or to the side of) optical or magnetic read sensors 164 as shown in FIGS. 13 and 14. In some embodiments, read sensors 164 are positioned on base 104 as shown in FIG. 13 when position indicator 158 is located on a bottom surface of sample rack 102. As shown in FIGS. 13 and 14, for example, each lane within housing 101 of sample bay 100 includes optical or magnetic read sensors 164 configured to sense a position indicator 158 on a sample rack 102 that is moving along the corresponding lane. In some embodiments in which an optical encoder strip or a magnetic encoder strip is fixed to top surface 162 of cover 146, the measurement system can include optical or magnetic read sensors 164 positioned on top panel 116 that are configured to read an optical encoder strip or a magnetic encoder strip 158 as sample rack 102 passes sensors 164, as shown in FIG. 14. In other embodiments in which position indicator 158 is an optical encoder strip fixed to side surface 161, the measurement system can include through-beam sensors 165 that generate a beam aligned with position indicator 158 to read optical encoder strip 158. In some embodiments in which position indicator 158 is a plurality of repeating recesses formed on sample rack 102, the measurement system can include a position sensor that includes a gear 166 which engages the plurality of corresponding recesses formed on sample rack 102, as shown in FIG. 15. As sample rack 102 moves between positions along the lane within housing 101 of sample bay 100, gear 166 rotates to encode the absolute position of sample rack 102. In some embodiments in which position indicator 158 is a friction strip affixed to sample rack 102, the measurement system can include a position sensor that includes a friction wheel, similar to gear 166 shown in FIG. 15, except without teeth and instead having a surface with a high coefficient of friction. As sample rack 102, having a friction strip 158, moves between positions along the lane within sample bay 100, the friction wheel engages the friction strip 158 and rotates to encode the absolute position of sample rack 102.

In some embodiments, the position measurement system is configured to determine the incremental position of sample rack 102.

Figure 12:
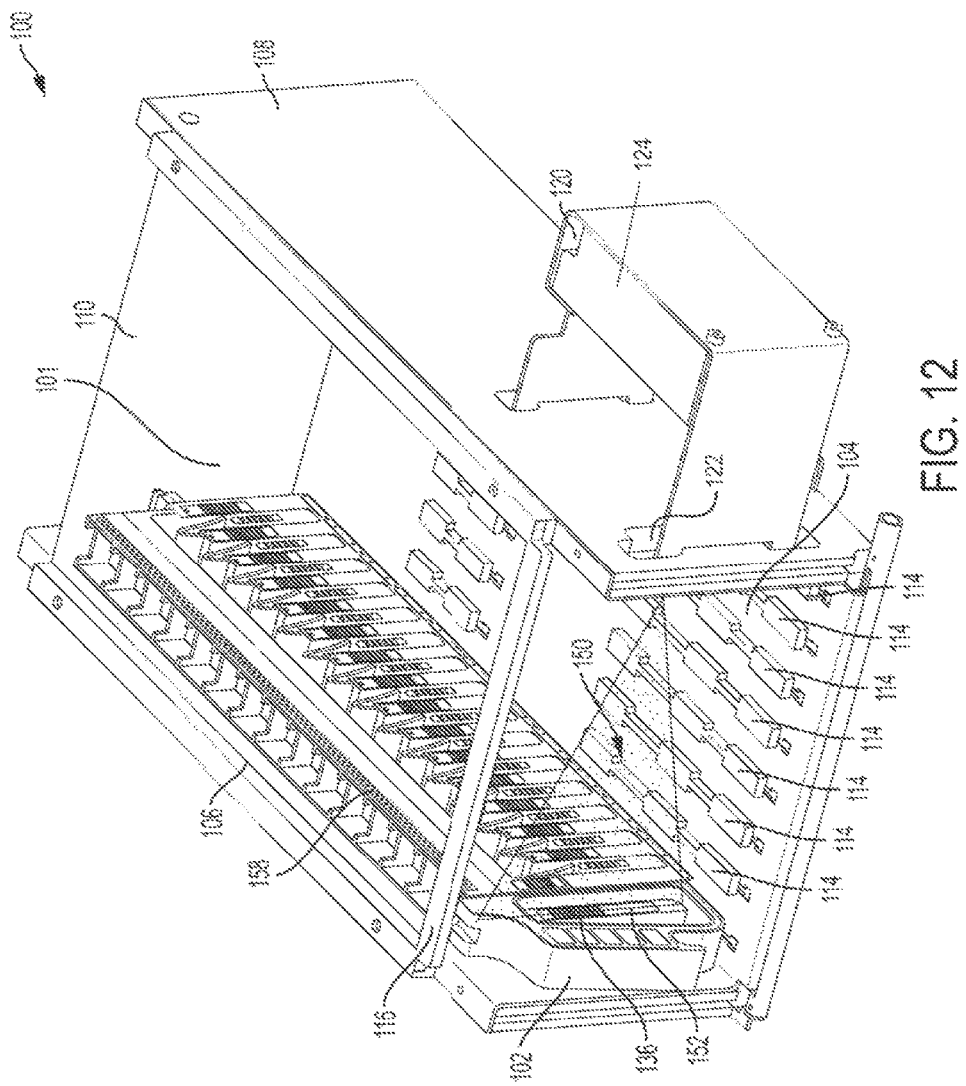
FIG. 12 illustrates a front perspective view of the sample bay of FIG. 11 with a rack fully inserted into a housing of the sample bay according to an embodiment.

Referring to FIGS. 11 and 12, in some embodiments, reader 124 has an optical path 150 and is configured to read a label at an object plane 152 along optical path 150. In some embodiments, the working distance range of reader 124 is large enough to include each lane defined in housing 101, along which sample racks 102 move. In some embodiments in which reader 124 is a camera, reader 124 is a charge-coupled device (CCD) or complementary metal-oxide-semiconductor (CMOS) camera. In some camera embodiments, reader 124 is a line scan or an area scan camera. In some camera embodiments, reader 124 has a field of view height sufficient to read a label, for example, label 144, on sample rack 102 at each lane of housing 101. In some camera embodiments, reader 124 samples at a rate sufficient to acquire an image of a label, for example, label 144, on sample rack 102 moving at a rate up to at least 1000 mm/sec, including for example 100 mm/sec, 300 mm/sec, 500 mm/sec, and 600 mm/sec. For example, in some embodiments, reader 124 samples at a rate of at least 35 Hz, such as 50 Hz or 60 Hz. For example, reader 124 can be a CMOS, line scan camera having a working distance range that includes each lane of housing 101 along which sample racks 102 move, a field of view greater than a height of sample rack 102, and a sample rate of at least 60 Hz.

In some embodiments in which reader 124 is a camera, as a sample rack 102 is inserted into sample bay 100 along a lane defined by guides 114 (and in direction 148), reader 124 is configured to acquire images of sample rack 102 as it passes through object plane 152. For example, the acquired images can include images of labels 138, 140, 144, 137, and 136, that pass through object plane 152 of reader 124. In some embodiments, the acquired images are transmitted to a processing and control unit configured to process the acquired images to decode information contained in labels 138, 140, 144, 137, and 136 of the acquired images. In some embodiments, the processing and control unit is coupled to or disposed in housing 101. In some embodiments, this image decoding occurs after sample rack 102 is fully inserted into housing 101 of sample bay 100. In some embodiments, decoding the acquired images after sample rack 102 is fully inserted allows camera reader 124 to have a higher sample rate. For example, with such post-processing, camera reader 124 can have a sample rate of at least 30 frames per second and, in some embodiments, at least 60 frames per second. In some embodiments, the processing and control unit is configured to decode a one-to-three second video stream captured by camera reader 124 after the images are acquired (in contrast to real-time decoding), which can increase the sample rate.

In some embodiments, in which position indicator 158 on sample rack 102 is an optical encoder strip, reader 124 can be configured to acquire images of the optical encoder strip in addition to acquiring images of labels 138, 140, 144, 137, and 136. The acquired images of optical encoder strip 158 can be transmitted to the processing and control unit, and the processing and control unit decodes the acquired images of the optical encoder strip to determine the absolute position of sample rack 102 within housing 101 of sample bay 100. In such embodiments, reader 124 can be a line scan camera. In some line scan camera embodiments, reader 124 has at least a 5 μm pixel resolution (e.g., 7 μm pixel resolution) and that samples at a rate of at least 50 frames per second (for example, 60 or 80 frames per second). For example, a line scan camera reader 124 that samples at a rate of 60 frames per second can capture an image about every 10 μm when sample rack 102 moves at a rate of 600 mm/sec. In some line scan camera embodiments, reader 124 has at least 1500 pixels (e.g., 2000 pixels) and a field of view of at least 50 mm (e.g., 100 mm). For example, when line scan camera reader 124 has 2000 pixels and a field of view of 100 mm, each of the pixel images is about 50 μm. In some embodiments, the optical encoder strip includes a plurality of lines having widths that cover at least three pixels of a line scan camera reader 124. In some line scan camera embodiments, line scan camera reader 124 has a working distance in the range of 200 mm to 300 mm.

In some embodiments, sample rack 102 is moved between a first position in housing 101 of sample bay 100 to a second position in housing 101 of sample bay 100. The first position can be, for example, when sample rack 102 first engages guides 114 on base 104 of housing 101, and the second position can be, for example, any position between the first position and a position at which sample rack 102 is fully inserted in housing 101.

In some embodiments, the user manually moves sample rack 102 between the first and second positions. When manually inserted, sample rack 102 can be moved at a rate that exceeds 100 mm/sec, for example, rates that exceed 300 mm/sec, 500 mm/sec, 600 mm/sec, or 1000 mm/sec.

As sample rack 102 is moved between the first position and the second position in housing 101, a position measurement system, for example, any one of the above described embodiments of a position measurement system, measures the absolute position of sample rack 102 in some embodiments. Also, as sample rack 102 is moved between the first position and the second position, reader 124 acquires images of sample rack 102, including images of machine-readable labels 144 of sample receptacle 128, at object plane 152 of reader 124. Reader 124 transmits the acquired images to the processing and control unit that decodes the acquired images, including decoding the acquired images of machine-readable labels 144 on each sample receptacle 128 passing through object plane 152. In some embodiments, decoding the acquired images comprises processing the acquired images to determine if the acquired images include a machine-readable label and, if they do, extracting the information contained in the machine-readable label. In some embodiments, this decoding occurs after sample rack 102 is fully inserted within housing 101 of sample bay 100.

In some embodiments, the processing and control unit determines the speed at which sample rack 102 is moved between first and second positions in housing 101. For example, in embodiments using an optical encoder strip, the processing and control unit processes the acquired images to determine the rack insertion speed. In some embodiments, the processing and control unit also associates information decoded from an acquired image of the machine-readable label 144 with the corresponding sample receptacle 128 based on the measured absolute position of sample rack 102 when the decoded image of the machine-readable label 144 was acquired. The processing and control unit can store this association into a memory of the system.

In some embodiments, the processing and control unit decodes information from an acquired image of the machine-readable label 144 and associates the decoded information with the corresponding sample receptacle 128 without acquiring an image of pocket identifier 138 on sample rack 102. For example, the processing and control unit can be configured to activate reader 124 when sample rack 102 is at predetermined positions that correspond to when the center of each pocket 130 of sample rack 102 is aligned with object plane 152 of reader 124, when rack identifier 136 is aligned with object plane 152 of reader 124, and when cover identifier 137 is aligned with object plane 152. At these predetermined positions, reader 124 acquires images of empty-recess identifier 140 or two-dimensional barcode 144, rack identifier 136, and cover identifier 144, respectively. The processing and control unit can also deactivate reader 124 when sample rack 102 is not at the predetermined positions that correspond to when the center of each pocket 130 of sample rack 102 is aligned with object plane 152 of reader 124, when rack identifier 136 is aligned with object plane 152 of reader 124, and when cover identifier 137 is aligned with object plane 152. That is, activation of reader 124 is modulated based on the position of sample rack 102. In such embodiments, reader 124 can be a two-dimensional barcode reader, for example, a laser barcode reader, having a sample rate less than 35 scans per second, for example, a scan rate of about 16-32 scans per second, even when sample rack 102 is traveling at speeds exceeding 100 mm/sec, for example, speeds exceeding 500 mm/sec—speeds associated with manual insertion of sample rack 102 within sample bay 100. In some embodiments, sample rack 102 moves at a speed up to 1000 mm/sec. In such embodiments, the measured position of sample rack 102 is determined by a position measurement system having a sensor separate from reader 124. For example, the measured position of sample rack 102 can be determined using position indicators 158 (for example, a pattern of recesses or protrusions, an optical encoder tape, a magnetic encoder tape, a capacitive strip) and position sensors (for example, optical or magnetic read sensors 164, gear or friction wheel 166, or through-beam sensors 165) as described above. Determining the position of sample rack 102 using position indicators 158 and position sensors 164, 165, or 166, separate from reader 124, can help minimize the necessary performance requirements of reader 124. In some embodiments, the processing and control unit is also configured to activate light source 125 when sample rack 102 is at each of the plurality of predetermined positions-simultaneously when acquiring the image with reader 124. Using light source 125 when acquiring the image can further reduce the necessary performance requirement of reader 124.

In some embodiments, this method of associating information from a decoded acquired image of the machine-readable label 144 with the corresponding sample receptacle 128 is used when manually moving sample rack 102 between the first and second positions in housing 101, for example, when the sample rack 102 is moving at a rate of at least 100 mm/sec (e.g., at least 300 mm/sec or 500 mm/sec and as fast as 1000 mm/sec).

Figure 18:
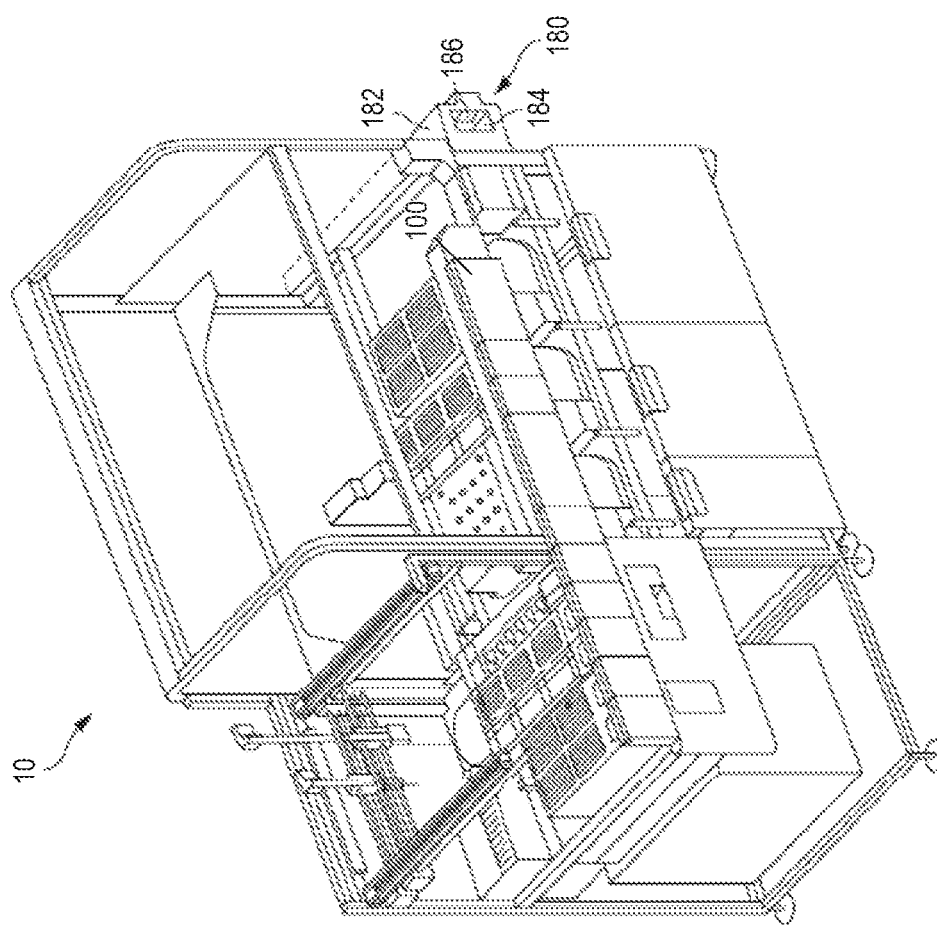
FIG. 18 illustrates a front perspective view of an analyzer system having a sample bay and a separate compartment for imaging a sample rack.

Referring to FIG. 18, in some embodiments, an analyzer system 10 includes a sample bay 100 having a reader 124, and a second module 180 that is separate from sample bay 100. In some embodiments, second module 180 defines a compartment 184 configured to receive at least one sample rack 102. Second module 180 also has a second reader 186 separate from reader 124 of sample bay 100. In some embodiments, sample bay 100 and second module 180 are enclosed in separate housings that are coupled together-housing 182 of second module 180 is separate from the housing defining sample bay 100 as shown in FIG. 18. In other embodiments, sample bay 100 and second module 180 are enclosed within the same housing, but the compartments of each sample bay 100 and second module 180 are separated by a wall.

Second reader 186 is configured to read a machine-readable label, for example, rack identifier 136, cover identifier 137, and two-dimensional barcode 144 on each sample receptacle 128, when inserted within second module 180. In some embodiments, second reader 186 is configured to read two-dimensional barcode 144 on each sample receptacle 128 as sample rack 102 is inserted within compartment 184 of second module 180. In other embodiments, second reader 186 is configured to scan sample rack 102 to read two-dimensional barcode 144 for each sample receptacle 128 after sample rack 102 is inserted. The acquired images are transmitted to the processing and control unit to be decoded.

After acquiring the images of the barcodes, including two-dimensional barcodes 144 on receptacles 128 of sample rack 102, in second module 180, a user can manually remove sample rack 102 from second module 180 and insert the same sample rack 102 in sample bay 100. In some embodiments, barcode reader 124 (for example, a one-dimensional laser barcode reader) does not read barcodes 144 on receptacles 128 as sample rack 102 is inserted along an available lane in sample bay 100. Instead reader 124 only reads rack identifier 136 (for example, a one-dimensional barcode) to confirm the sample rack 102 that was just scanned in second module 180 was inserted in sample bay 100. Reader 124 can also read cover identifier 137 to ensure the presence and proper positioning of cover 146. The processing and control unit can then associate the information decoded from the acquired images of two-dimensional barcodes 144 at second module 180 with the rack identifier 136 of sample rack 102 inserted in sample bay 100. In some embodiments, the processing and control unit can be configured to erase or otherwise disable reader 124 if sample rack 102 is not inserted into sample bay 100 within a predetermined time period, for example, 5 seconds. Thus, if sample rack 102 is not moved to sample bay 100 within the predetermined time period, the processing and control unit will not recognize sample rack 102 as having been previously scanned in the second module 180, and sample rack 102 will have to be scanned again in second module 180. This timing requirement can help minimize the risk that one or more un-scanned receptacles are switched for scanned receptacles 128 in the time between removing sample rack 102 from second module 180 and inserting sample rack 102 into sample bay 100. In some embodiments, reader 124 is configured only to read one-dimensional barcode labels, and second reader 186 is configured to read one- and two-dimensional barcodes. In some embodiments in which rack identifier 136 is an RFID tag, system 10 includes an RFID reader in sample bay 100 configured to interrogate sample rack 102 having an RFID tag.

Figure 17:
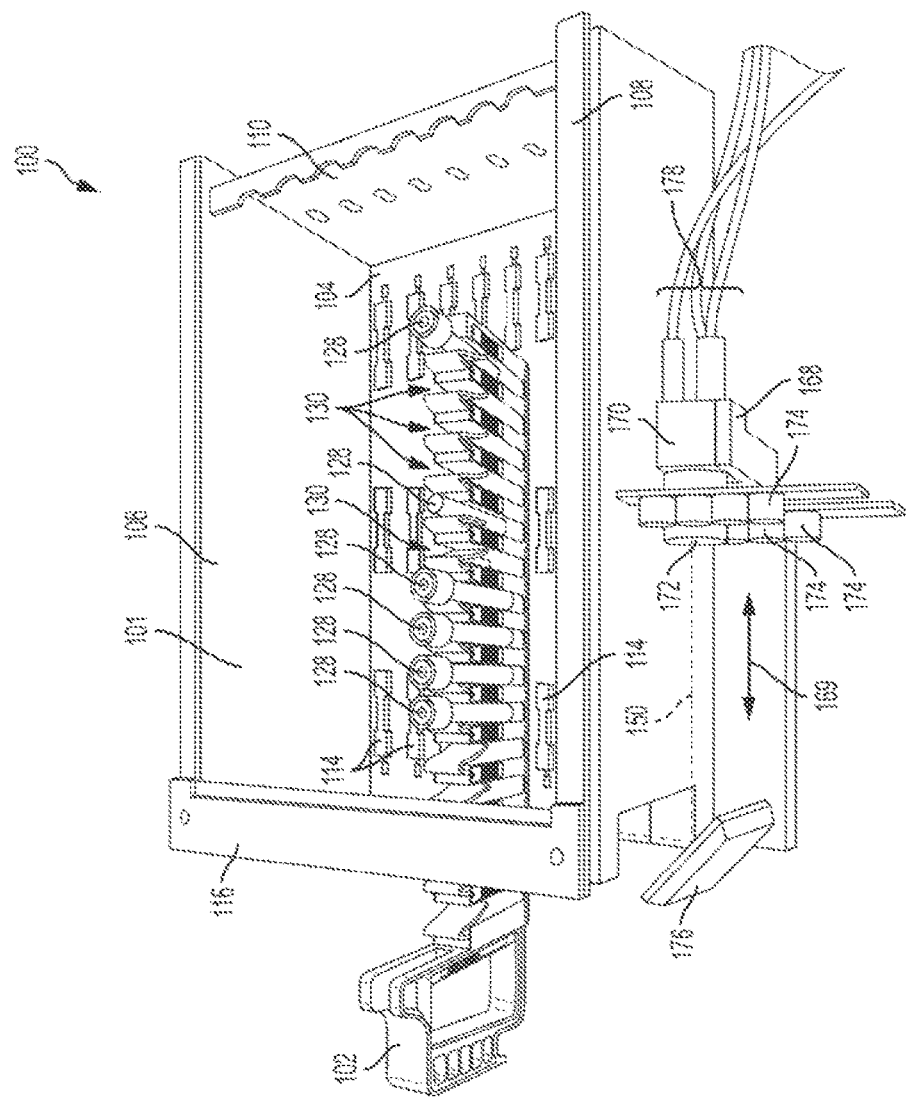
FIG. 17 illustrates a side perspective view of a sample bay according to still yet another embodiment.

Referring to FIG. 17, in some embodiments, sample bay 100 includes a reader support 168 that is moveable relative to the lanes along which sample racks 102 move within housing 101 of sample bay 100. In some embodiments, sample bay 100 includes a camera 170 fixedly coupled to reader support 168 such that camera 170 moves along with reader support 168. In some embodiments, camera 170 has a fixed focal length. In other embodiments, camera 170 has a variable focal length. The sample bay 100 can include an actuator that moves reader support 168 along a path 169 such that object plane 152 of camera 170 is operatively aligned with a lane having the sample rack 102 being imaged. In some embodiments, the actuator is a linear actuator such as mechanical, hydraulic, pneumatic, piezo-electric, and electro-mechanical linear actuators, for example. In some embodiments, reader support 168 is configured to move along path 169 in a range from about 150 mm to about 350 mm. Reader support 168 is configured such that object plane 152 of camera 170 can be aligned with each lane within sample bay 100. In some embodiments, path 169 of reader support 168 is parallel to the lanes along which sample racks 102 move within sample bay 100. In some embodiments, camera 170 is a CCD or CMOS camera. In some embodiments, camera 170 acquires images at a rate of at least 35 frames per second. For example, camera 170 can acquire images at a rate of 60 frames per second. In some embodiments, the direction of an optical path 150 from a lens 172 of camera 170 is bent. For example, as shown in FIG. 17, bay 100 can include a mirror 176 that bends optical path 150 towards the lanes along which sample racks 102 move. For example, as shown in FIG. 17, mirror 176 bends optical path 150 ninety degrees towards the lanes of sample bay 100. In other embodiments, mirror 176 bends optical path 150 at other angles more than or less than ninety degrees. In some embodiments, sample bay 100 includes a light source 174 configured to illuminate the lanes within sample bay 100. In some embodiments, light source 174 is also coupled to reader support 168 such that light source 174 moves along with reader support 168 and camera 170. In some embodiments, the optical path of light waves emitted from light source 174 coincides with optical path 150 of camera 170. Light source 174 can be one or more LEDs in some embodiments. In some embodiments, as shown in FIG. 17, light source 174 comprises eight LEDs—for example, four above lens 172 of camera 170 and four below lens 172. In other embodiments, light source 174 comprises four LEDs—for example, two above lens 172 and two below lens 172. In embodiments in which light source 174 comprises LEDs, the number and configuration of the LEDs may vary to achieve the desired illumination within sample bay 100. In some embodiments, light source 174 is incorporated into camera 170.

In use, sample rack 102 is moved between a first position and a second position along a first lane in housing 101 of sample bay 100. For example, sample rack 102 is manually moved along the first lane. The first position can be, for example, the position at which sample rack 102 engages guides 114 on base 104, and the second position can be, for example, a position between the first position and a position at which sample rack 102 is fully inserted within sample bay 100. As sample rack 102 moves between the first position and the second position along the lane, camera 174 acquires images of machine-readable label 144 on sample receptacles 128 supported by sample rack 102. The acquired images are transmitted to the processing and control unit to be decoded. The acquired images can be decoded after sample rack 102 is fully inserted within sample bay 100. Another sample rack 102 can be moved, for example, manually, between a first position and a second position along a different lane within a housing of sample bay 100. The processing and control unit controls the actuator coupled to reader support 168 to move reader support 168 and, thus, position the object plane 152 of camera 170 at the second lane along which the second sample rack 102 is moving. As the second sample rack 102 moves between the first position and the second position along the lane, camera 170 acquires images of machine-readable label 144 on sample receptacles 128 supported by the second sample rack 102. The acquired images are transmitted to the processing and control unit to be decoded. The acquired images of the second sample rack 102 can be decoded after sample rack 102 is fully inserted within sample bay 100.

In some embodiments, camera 170 samples at a rate of 60 frames per second and has a 1/10,000 second shutter speed when using light source 174 to strobe the interior of housing 101. In some embodiments, camera 170 has a working distance of 250 mm. In some embodiments, camera 170 has a focal distance of at least ±10 mm from the focal plane. In some embodiments, camera 170 has a field of view that is 80 mm tall and 25 mm wide. In some embodiments, camera 170 has 1600×1200 pixels.

In some embodiments, the processing and control unit activates light source 174 simultaneously when acquiring the images of machine-readable label 144 of each sample receptacle 128 supported on the first and second sample racks 102.

In some embodiments, camera 170 and light source 174 are operatively coupled to the processing and control unit through one or more cables 178. For example, the images acquired by camera 170 can be transmitted to the processing and control unit via one of the plurality of cables 178. And for example, the control signals that activate light source 174 can be transmitted from the processing and control unit to light source 174 via one of the plurality of cables 178. In some embodiments, one of the plurality of cables 178 is operatively coupled to an actuator that moves support 168.

In any of the above disclosed embodiments, a user can insert sample rack 102 into housing 101. For example, the user can align guide track 156 of sample rack 102 with guide 113 formed on base 104 of housing 101. From this first position, the user can manually move sample rack 102 along the lane defined by guide 114 to a fully inserted position within housing 101. As sample rack 102 is moved to the fully inserted position, reader 124 reads labels on sample rack 102, for example, two-dimensional labels 144 on sample receptacles 128 held by sample rack 102. In some embodiments, after sample rack 102 is fully inserted, the processing and control unit decodes the read labels to extract information, for example, the specific assay to perform and patient information. And, after sample rack 102 is inserted into sample bay 10, sample material contained in sample receptacles 128 carried in the sample rack 102 can be accessed via a fluid transfer mechanism-such as the probe (e.g., a barrel with a protective tip, such as a pipette tip, mounted thereon) of an automated, robotically operated pipetting device through the access openings 126 formed in top panel 116. Analyzer system 10 then performs the assay as indicated in the decoded information from, for example, two-dimensional barcode 144.

Some embodiments are implemented via control and computing hardware components, user-created software, data input components, and data output components. Hardware components include, for example, the processing and control unit (e.g., system controller(s)), such as microprocessors and computers, configured to effect computational and/or control steps by receiving one or more input values, executing one or more algorithms stored on non-transitory machine-readable media (e.g., software) that provide instruction for manipulating or otherwise acting on the input values, and output one or more output values. Such outputs may be displayed or otherwise indicated to an operator for providing information to the operator, for example information as to the status of the instrument or a process being performed thereby, or such outputs may comprise inputs to other processes and/or control algorithms. Data input components comprise elements by which data is input for use by the control and computing hardware components. Such data inputs may comprise positions sensors, motor encoders, as well as manual input elements, such as graphic user interfaces, keyboards, touch screens, microphones, switches, manually-operated scanners, voice-activated input, etc. Data output components may comprise hard drives or other storage media, graphic user interfaces, monitors, printers, indicator lights, or audible signal elements (e.g., buzzer, horn, bell, etc.). In some embodiments, the processing and control unit can comprises a single module that performs image processing and system control. In other embodiments, the processing and control unit comprises a plurality of modules that perform discrete processing and control steps. In some embodiments, the image processing module can be a component of reader 124 that processes (for example, post-processing) images stored in a buffer of reader 124.

Software comprises instructions stored on non-transitory computer-readable media which, when executed by the control and computing hardware, cause the control and computing hardware to perform one or more automated or semi-automated processes. In some embodiments, the software for image processing is stored in memory on reader 124, for example. In some embodiments, the software for image processing is stored in external memory in communication with the processing and control unit.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method of reading machine-readable labels on sample receptacles, comprising:
   moving a first sample rack between a first position and a second position along a first lane in a housing, the first sample rack holding a first plurality of sample receptacles, wherein each sample receptacle of the first plurality of sample receptacles has a machine-readable label;
   moving a camera to focus the camera at a point along the first lane;
   with the camera, reading the machine-readable label of each sample receptacle of the first plurality of sample receptacles held by the first sample rack as the first sample rack moves between the first position and the second position;
   moving a second sample rack between a first position and a second position along a second lane different than the first lane in the housing, the second sample rack holding a second plurality of sample receptacles, wherein each sample receptacle of the second plurality of sample receptacles has a machine-readable label;
   moving the camera to focus the camera at a point along the second lane; and
   with the camera, reading the machine-readable label of each sample receptacle of the second plurality of sample receptacles held by the second sample rack as the second sample rack moves between the first position and the second position.

2. The method of claim 1, wherein the camera is a fixed focal length camera.

3. The method of claim 1, wherein the camera is a variable focal length camera.

4. The method of claim 1, wherein moving the first sample rack comprises manually moving the first sample rack, and wherein moving the second sample rack comprises manually moving the second sample rack.

5. The method of claim 1, wherein moving the first sample rack comprises automatically moving the first sample rack, and wherein moving the second sample rack comprises automatically moving the second sample rack.

6. The method of claim 1, further comprising activating a light source simultaneously with reading the machine-readable label of each sample receptacle of the first plurality of sample receptacles held by the first sample rack as the first sample rack moves between the first position and the second position, and activating the light source simultaneously with reading the machine-readable label of each sample receptacle of the second plurality of sample receptacles held by the second sample rack as the second sample rack moves between the first position and the second position.

7. The method of claim 1, further comprising reading with the camera a rack-identifying, machine-readable label on each of the first and second sample racks.

8. The method of claim 1, wherein the machine-readable label of each sample receptacle of the first and second plurality of sample receptacles comprises a two-dimensional barcode.

9. The method of claim 8, wherein the two-dimensional barcode of each sample receptacle of the first and second plurality of sample receptacles contains information that associates a sample contained in the sample receptacle with a patient.

10. The method of claim 1, wherein:
    reading the machine-readable label of each sample receptacle of the first plurality of sample receptacles held by the first sample rack comprises acquiring first images along an optical path of the camera;
    reading the machine-readable label of each sample receptacle of the second plurality of sample receptacles held by the second sample rack comprises acquiring second images along the optical path of the camera; and
    a portion of the optical path is fixed relative to the first lane and the second lane.

11. The method of claim 10, wherein the first images are acquired at a rate of at least 35 Hz, and wherein the second images are acquired at a rate of at least 35 Hz.

12. The method of claim 1, wherein:
    reading the machine-readable label of each sample receptacle of the first plurality of sample receptacles held by the first sample rack comprises acquiring first images along an optical path of the camera;
    reading the machine-readable label of each sample receptacle of the second plurality of sample receptacles held by the second sample rack comprises acquiring second images along the optical path of the camera; and the first lane is situated between the second lane and the camera along the optical path of the camera.

13. A system for reading machine-readable labels on sample receptacles, comprising:
a housing defining at least a first lane and a second lane, each lane being configured to receive a sample rack adapted to hold a plurality of sample receptacles; and
a camera configured to move to a first position that focuses the camera at a first position along the first lane and to a second position that focuses the camera at a second position along the second lane, the camera being configured to acquire an image of a machine-readable label of each sample receptacle of a first plurality of sample receptacles held by a first sample rack moving along the first lane and an image of a machine-readable label of each sample receptacle of a second plurality of sample receptacles held by a second sample rack moving along the second lane.

14. The system of claim 13, wherein the camera is a fixed focal length camera.

15. The system of claim 13, wherein the camera is a variable focal length camera.

16. The system of claim 13, wherein the camera is configured to acquire images of the machine-readable label of each sample receptacle of the first plurality of sample receptacles as the first sample rack is manually received by the first lane, and wherein the camera is configured to acquire images of the machine-readable label of each sample receptacle of the second plurality of sample receptacles as the second sample rack is manually received by the second lane.

17. The system of claim 13, wherein the camera is configured to acquire images of the machine-readable label of each sample receptacle of the first plurality of sample receptacles as the first sample rack is automatically received by the first lane, and wherein the camera is configured to acquire images of the machine-readable label of each sample receptacle of the second plurality of sample receptacles as the second sample rack is automatically received by the second lane.

18. The system of claim 13, wherein the machine-readable label of each sample receptacle of the first and second plurality of sample receptacles comprises a two-dimensional barcode.

19. The system of claim 18, wherein the two-dimensional barcode of each sample receptacle of the first and second plurality of sample receptacles contains information that associates a sample contained in the sample receptacle with a patient.

20. The system of claim 13, wherein the camera is a CCD camera or a CMOS camera.

21. The system of claim 13, further comprising a light source configured to illuminate the machine-readable label of each sample receptacle within the housing.

22. The system of claim 21, further comprising a moveable stage, wherein the camera and the light source are coupled to the stage.

23. The system of claim 13, wherein the camera is configured to move along a lane parallel to the first lane and the second lane.

24. The system of claim 13, further comprising a mirror positioned along an optical path between the camera and the first position on the first lane and the second position on the second lane.

25. The system of claim 13, wherein a portion of an optical path of the camera is fixed relative to the first lane and the second lane.

26. The system of claim 13, wherein the first lane is situated between the second lane and the camera along an optical path of the camera.

27. The system of claim 13, wherein the camera is configured to to acquire images at a rate of at least 35 Hz.

* * * * *

UNITED STATES PATENT AND TRADEMARK OFFICE
CERTIFICATE OF CORRECTION

PATENT NO. : 10,146,973 B2
APPLICATION NO. : 15/092150
DATED : December 4, 2018
INVENTOR(S) : Hagen et al.

It is certified that error appears in the above-identified patent and that said Letters Patent is hereby corrected as shown below:

In the Claims

In Column 24, Claim 27, Line 36, delete "to to acquire" and insert -- to acquire --, therefor.

Signed and Sealed this
Fifth Day of February, 2019

Andrei Iancu
*Director of the United States Patent and Trademark Office*